(12) United States Patent
McGuinness et al.

(10) Patent No.: US 11,866,510 B2
(45) Date of Patent: *Jan. 9, 2024

(54) CHIMERIC ANTIGEN RECEPTOR WITH SINGLE DOMAIN ANTIBODY

(71) Applicant: CRESCENDO BIOLOGICS LIMITED, Cambridge (GB)

(72) Inventors: Brian McGuinness, Cambridge (GB); Colette Johnston, Cambridge (GB)

(73) Assignee: CRESCENDO BIOLOGICS LIMITED, Cambridge (GB)

( * ) Notice: Subject to any disclaimer, the term of this patent is extended or adjusted under 35 U.S.C. 154(b) by 728 days.

This patent is subject to a terminal disclaimer.

(21) Appl. No.: 16/099,099

(22) PCT Filed: May 8, 2017

(86) PCT No.: PCT/GB2017/051272
§ 371 (c)(1),
(2) Date: Nov. 5, 2018

(87) PCT Pub. No.: WO2017/191476
PCT Pub. Date: Nov. 9, 2017

(65) Prior Publication Data
US 2019/0144561 A1 May 16, 2019

(30) Foreign Application Priority Data
May 6, 2016 (GB) .................................. 1607968

(51) Int. Cl.
| | | |
|---|---|---|
| *C07K 14/705* | (2006.01) | |
| *C12N 5/0783* | (2010.01) | |
| *A61K 35/17* | (2015.01) | |
| *A61P 35/00* | (2006.01) | |
| *A61K 39/00* | (2006.01) | |
| *C07K 16/30* | (2006.01) | |
| *C07K 16/00* | (2006.01) | |

(52) U.S. Cl.
CPC .......... *C07K 16/3069* (2013.01); *A61K 35/17* (2013.01); *A61K 39/0011* (2013.01); *A61P 35/00* (2018.01); *C07K 16/00* (2013.01); *C12N 5/0646* (2013.01); *A61K 2039/5158* (2013.01); *C07K 2317/569* (2013.01); *C07K 2319/03* (2013.01)

(58) Field of Classification Search
None
See application file for complete search history.

(56) References Cited

U.S. PATENT DOCUMENTS

| 10,975,161 | B2 * | 4/2021 | Balloi ................ A61K 47/6425 |
|---|---|---|---|
| 11,236,174 | B2 | 2/2022 | Mcguinness et al. |
| 2010/0122358 | A1 | 5/2010 | Brueggemann et al. |
| 2019/0023807 | A1 | 1/2019 | Balloi et al. |
| 2020/0131274 | A1 | 4/2020 | Royle et al. |
| 2020/0362051 | A1 | 11/2020 | Brucklacher-Waldert et al. |
| 2020/0392244 | A1 * | 12/2020 | Balloi ................ A61K 47/6425 |
| 2022/0112305 | A1 | 4/2022 | Mcguinness et al. |

FOREIGN PATENT DOCUMENTS

| CN | 103087171 A | 5/2013 |
|---|---|---|
| CN | 103333249 A | 10/2013 |
| CN | 104159909 A | 11/2014 |
| CN | 105384825 | 3/2016 |
| CN | 105968203 A | 9/2016 |
| CN | 105968204 A | 9/2016 |
| CN | 105968205 A | 9/2016 |
| EP | 2363404 B1 | 9/2016 |
| WO | 2006089230 A2 | 8/2006 |
| WO | 2007117264 | 10/2007 |
| WO | 2013045916 A1 | 4/2013 |
| WO | 2013126712 A1 | 8/2013 |
| WO | 2014141192 | 9/2014 |
| WO | 2014198223 A1 | 12/2014 |
| WO | 2015142675 | 9/2015 |
| WO | 2015143079 A1 | 9/2015 |
| WO | 2016/025880 * | 2/2016 |
| WO | 2017122018 | 7/2017 |
| WO | 2017122019 | 7/2017 |
| WO | WO2017/122017 * | 7/2017 |
| WO | WO2017/122018 * | 7/2017 |
| WO | 2017191476 | 11/2017 |
| WO | 2019012260 A1 | 1/2019 |
| WO | 2019092451 A1 | 5/2019 |
| WO | 2019092452 A1 | 5/2019 |

OTHER PUBLICATIONS

Khan et al. Sci. Rep. (2017) 7, 45163; doi: 10.1038/srep45163 (12 pages).*
Zhu et al. Cell (2015) 161: 1280-1292.*
Lee et al. Nature Medicine (2016) 22: 1456-1464.*
Abdiche et al. mAbs (2016) 8: 264-277.*
Konitzer et al. mAbs (2017) 9: 536-549.*
Ferrara et al. mAbs (2015) 7: 32-41.*
Parola et al. Immunology (2018) 153: 31-41.*
Boyd et al. Current Opinion in Immunology 2016, 40: 103-109.*
Damschroder et al. Molecular Immunology (2004) 41: 985-1000.*
Van Regenmortel MHV. Front. Immunol. (2018) vol. 8, Article 2009 (11 pages).*
Kanyavuz et al. Nat Rev Immunol. 2019; 19(6): 355-368.*
Conroy et al. Methods (2017) 116: 12-22.*
Sheehan et al. Microbiol. Spectr. (2015) 3(1): AID-0028-2014; 17 pages.*
"U.S. Appl. No. 16/627,968; office action dated Oct. 4, 2021".
"Office Action corresponding to Chinese Application No. 201780039280.9 dated Sep. 23, 2021".

(Continued)

*Primary Examiner* — Ilia I Ouspenski
(74) *Attorney, Agent, or Firm* — Myers Bigel, P.A.

(57) ABSTRACT

The invention relates to chimeric antigen receptors (CAR) that comprise one or more single human variable domain antibody and cells that express such CAR. In particular, the invention relates to CARs that include multiple single human variable domain antibodies. In a particular embodiment, the one or more single human variable domain antibody binds to prostate membrane antigen.

13 Claims, 7 Drawing Sheets

Figure 1:
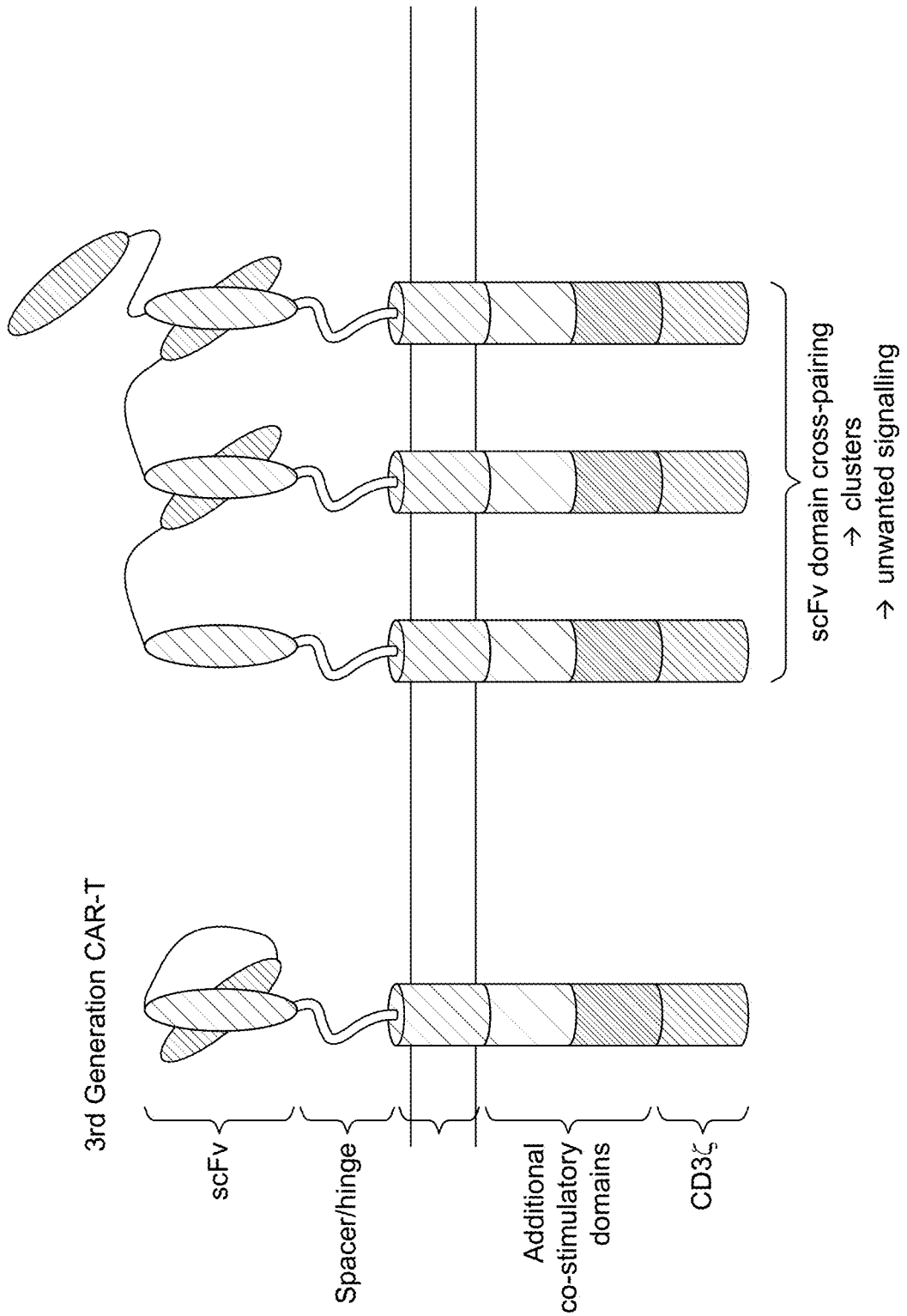

Specification includes a Sequence Listing.

(56) References Cited

OTHER PUBLICATIONS

"U.S. Appl. No. 16/069,495; office action dated Aug. 11, 2020".
"Crescendo Biologics: "Humabody fragments: Small and perfectly formed" Mar. 15, 2015 pp. BI2-BI3, Retrieved from the Internet: URL:http://www.crescendobiologics.com/uploads/news/id34/Crescendo0315.pdf".
"Examination Report corresponding to European Application No. 17700734.1 dated Jul. 24, 2020".
"Examination Report corresponding to European Application No. 17701006.3 dated Jun. 5, 2019".
Hamed, "Production of Nanobodies Against Prostate-Specific Membrane Antigen (PSMA) Recognizing LnCaP Cells. Research Gate. The International Journal of Biological Markers. Jan. 2014."
"International Preliminary Report on Patentability corresponding to International Application No. PCT/GB2017/050074 dated Jul. 26, 2018".
"International Preliminary Report on Patentability corresponding to International Application No. PCT/GB2017/050075 dated Jul. 26, 2018".
"International Preliminary Report on Patentability corresponding to International Application No. PCT/GB2017/051272 dated Nov. 15, 2018".
"International Preliminary Report on Patentability corresponding to International Application No. PCT/GB2018/051941 dated Jan. 23, 2020".
"International Search Report and Written Opinion corresponding to International Application No. PCT/GB2017/050074 dated May 30, 2017".
"International Search Report and Written Opinion corresponding to International Application No. PCT/GB2017/050075 dated Mar. 23, 2017".
"International Search Report and Written Opinion corresponding to International Application No. PCT/GB2017/051272 dated Sep. 11, 2017".
"International Search Report and Written Opinion corresponding to International Application No. PCT/GB2018/051941 dated Sep. 14, 2018.".
Bander, et al., ""Targeted Systematic Therapy of Prostate Cancer With a Monoclonal Antibody to Prostate-Specific Membrane Antigen", Semin Oncol. 30:667-677 (2003)".
Barve, et al., ""Prostate cancer relevant antigens and enzymes for targeted drug delivery", J Control Release 187:118-132 (2014)".
Bayachou, Mekki, et al., ""Catalytic Two-Electron Reductions of N2) and N3 by My globin in Surfactant Films" Inorg. Chemn. 2000, 39, 289-293."
Bruggemann, et al., ""A Repertoire of Monoclonal Antibodies With Human Heavy Chains From Transgenic Mice", Proceedings of the National Academy Sciences, National Academy of Sciences, vol. 86, No. 17, Sep. 1, 1989 (Sep. 1, 1989), pp. 6709-6713".
Chatalic, Kristen, et al., ""A Novel In-Labeled Anti-Prostate-Specific Membrane Antigen Nanobody for Targeted SPECT/CT Imaging ofProstate Cancer" The Journal of Nuclear Medicine. vol. 56, No. 7, Jul. 2015. p. 1094-1099."
Cizeau, et al., ": "Engineering and characterization of anti-PSMA humabody-deBouganin fusion proteins", Proceedings of the American Association for Cancer Research Annual Meeting 2018; Apr. 2018 (Apr. 2018), Retrieved from the Internet: URL:http://cancerres.aacrjournals.org".
Evazalipour, et al., ""Generation and characterization of nanobodies targeting PSMA for molecular imaging of prostate cancer", Contrast Media & Molecular Imaging 9(3):211-220 (2014)".
Evazalipour, Mehdi, et al., ""Camel Heavy Chain Antibodies Against Prostate-Specific Membrane Antigen" HYBRIDOMA. vol. 31, No. 6, 2012. p. 424-429."
Fan, Xiaozhu, et al., "Ultrasonic Nanobubbles Carrying Anti-PSMA Nanobody: Construction and Application in Prostate Cancer-Targeted Imaging. Plos One. Jun. 25, 2015. p. 1-13.".
Fatemeh Rahimi Jamnani, et al., ""T cells expressing VHH-directed oligoclonal chimeric HER2 antigen receptors: Towards tumor-directed oligocional T cell therapy", Biochimica Et Biophysica Acta (BB) General Subjects 1840 (1):378-386 (2014)".
Holt L J, et al., ""Domain antibodies: proteins for therapy", Trends in Biotechnology, Elsevier Publications, Cambridge, GB, vol. 21, No. 11, Nov. 1, 2003 (Nov. 1, 2003), pp. 484-490".
Matthias Di Huyvetter, et al., ""Radiolabeled nanobodies as theranostic tools in targeted radionuclide therapy off cancer", Expert Opinion On Drug Delivery, vol. 1-6, 49-8111, No. 12, Jul. 18, 2014 (Jul. 18, 2014), pp. 1939-1954".
McGuiness, et al., ""Multifunctional biologics for targeted T-cell therapy based on in vivo matured fully human VH domains", Proceedings of the American Association for Cancer Research Annual Meeting 2018; Apr. 2018 Retrieved from the Internet: URL:http://cancerres.aacrjour".
Rob C. Roovers, et al., ""A biparatopic anti-EGFR nanobody efficiently inhibits solid tumour growth", International Journal of Cancer, vol. 129, No. 8, Oct. 15, 2011 (Oct. 15, 2011), pp. 2013-2024".
Zare, et al., ""Production of nanobodies against prostate-specific membrane antigen (PSMA) recognizing LnCaP cells", Int J Biol Markers 29(2):e169-e179 (2014)".
"U.S. Appl. No. 16/069,497; office action dated May 12, 2021".
Bahara, Nur Hidaya Hairul, et al., "Construction of a Semisynthetic Human VH Single-Domain Antibody Library and Selection of Domain Antibodies against alpha-Crystalline of *Mycobacterium tuberculosis*", Journal of Biomolecular Screening 21(1):35-43 (Jan. 2016).
Chen, Longxin, et al., "Epitope-directed antibody selection by site-specific photocrosslinking", Science Advances 6 (14):eaaz7825 (Apr. 1, 2020) (9 pages).
Mncke, Cecile, et al., "Introduction to Heavy Chain Antibodies and Derived Nanobodies", Single Domain Antibodies. Methods in Molecular Biology (Methods and Protocols), vol. 911 https://doi.org/10.1007/978-1-61779-968-6_2 (Jul. 12, 2012).
"Examination Report corresponding to European Application No. 17724869.7 dated Dec. 4, 2019".
"Office Action corresponding to Japanese Application No. 2018-537519 dated Feb. 5, 2021".
"Office Action corresponding to Japanese Application No. 2018-537533 dated Feb. 16, 2021".
Conrath, Katja ELS, et al., "Camel Single-Domain Antibodies as Modular Building Units in Bispecific and Bivalent Antibody Constructs", The Journal of Biological Chemistry 276(10):7346-7350 (Mar. 2001).
Guo, Yelei, et al., "Chimeric Antigen Receptor-Modified T Cells for Solid Tumors: Challenges and Prospects", Journal of Immunology Research vol. 2016 (Feb. 21, 2016) 11 pages.
Vincke, Cecile, et al., "General strategy to Humanize a Camelid Single-domain Antibody and Identification of a Universal Humanized Nanobody Scaffold", The Journal of Biological Chemistry 284(5):3273-3284 (Jan. 30, 2009).
Zare, Hamed, et al., "Production of nanobodies against prostate-specific membrane antigen (PSMA) recognizing LnCaP cells", Int J Biol Markers 29(2):e169-e179 (2014).
"Office Action corresponding to Japanese Application No. 2020-500832 dated Sep. 2, 2022".
Hawkey, Nathan M, et al., "Prostate-specific membrane antigen-targeted theranostics: past, present, and future approaches", Clin Adv Hematol Oncol. 20(4):227-238 (Apr. 2022).
"Office Action corresponding to Japanese Application No. 2021-211614 dated May 26, 2023".
D'huyvetter, Matthias, et al., "Radiolabeled nariobodies as theranostic tools in targeted radionuclide therapy of cancer.", Expert Opin Drug Deliv 11(12):1939-54 (Dec. 2014).
Brown, McKay, et al., "Tolerance to Single, but Not Multiple, Amino Acid Replacements in Antibody VhCDR2", J Immunol 156(9):3285-3291 (May 1, 1996).
Muyldermans, Serge, "Nanobodies: Natural Single-Domain Antibodies", Annu. Rev. Biochem. 82.775-97 (Mar. 13, 2013).
Muyldermans, Serge, "Single domain camel antibodies: current status", Reviews in Molecular Biotechnology 74:277-302 (2001).
"Examination Report corresponding to European Application No. 17724869.7 dated Nov. 14, 2023".

(56) References Cited

OTHER PUBLICATIONS

Dong, Qi, et al., "110?IL-2 variant improves CAR-T functionality and efficacy against solid tumors", Journal for Immuno Therapy of Cancer 9(Suppl 2):A120 (Nov. 1, 2021) 1 page.

Jackaman, Connie, et al., "IL-2 Intratumoral Immunotherapy Enhances CD8 + T Cells That Mediate Destruction of Tumor Cells and Tumor Associated Vasculature: A Novel Mechanism for IL-2", The Journal of Immunology 171 (10):5051-5063 (Nov. 15, 2003).

Zuccolotto, Gaia, et al., "PSMA-Specific CAR-Engineered T Cells Eradicate Disseminated Prostate Cancer in Preclinical Models", PLos One 9(10):e109427 (Oct. 3, 2014) 12 pages.

* cited by examiner

IgG Antibody
150 kDa

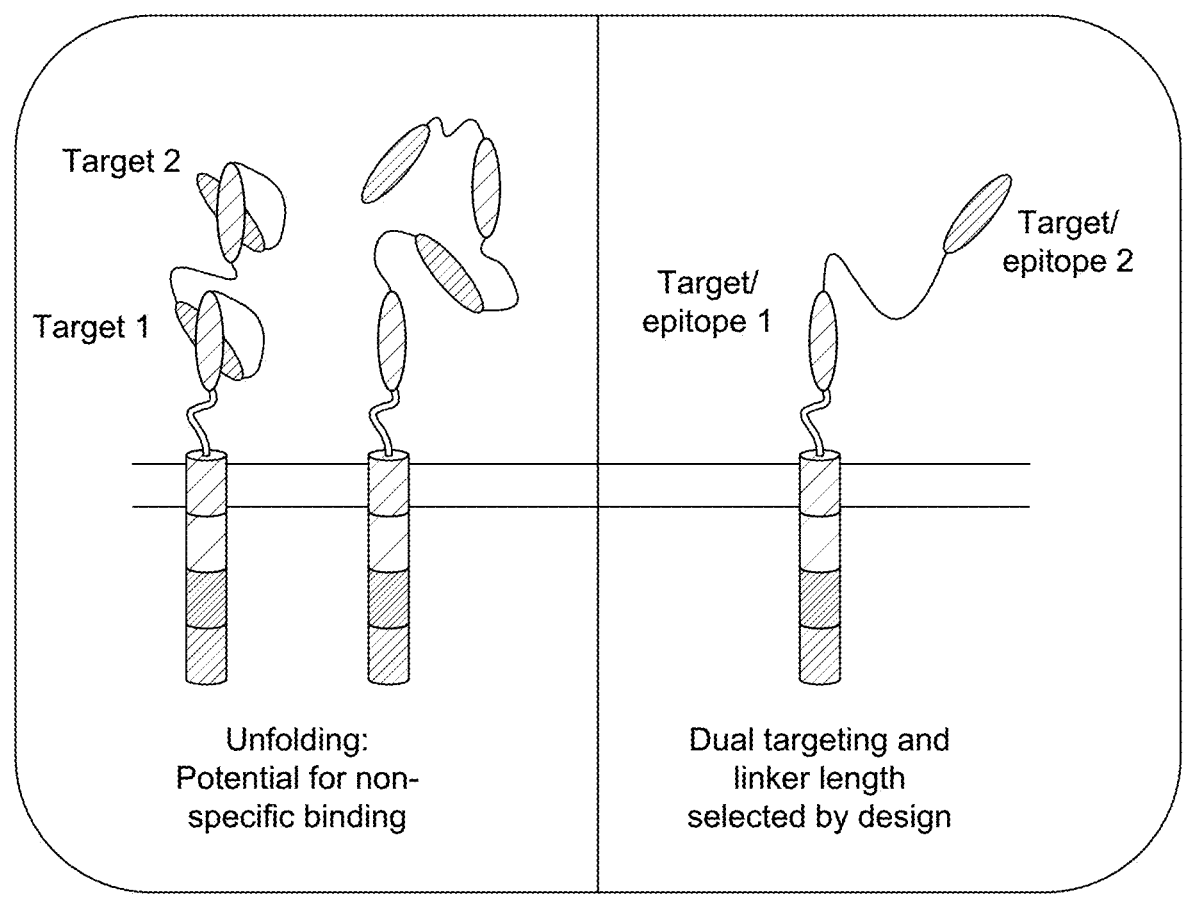
FIG. 3a
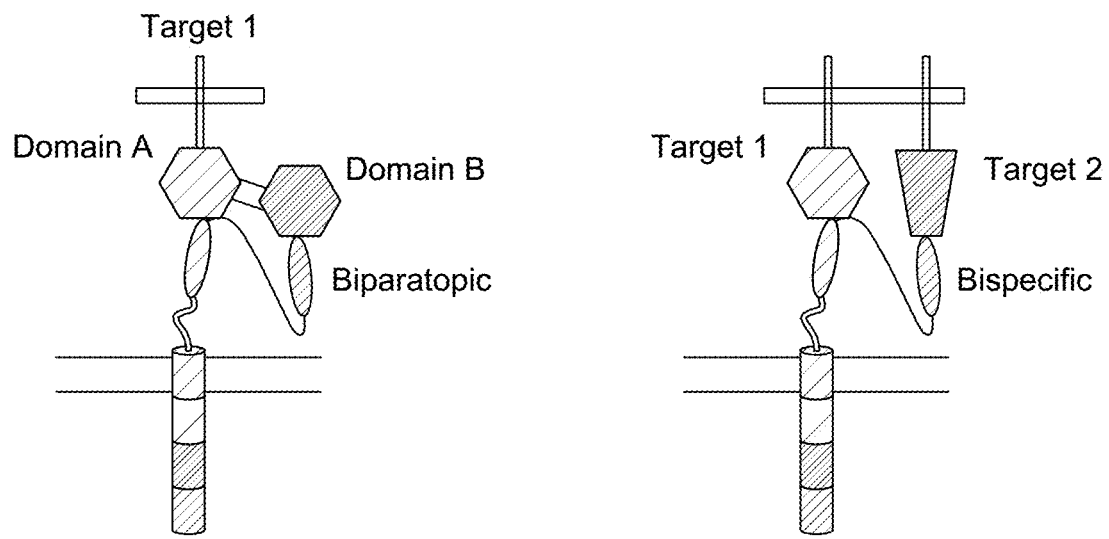
FIG. 3b
FIG. 3c

SEQUENCE LISTING

```
<160> NUMBER OF SEQ ID NOS: 34

<210> SEQ ID NO 1
<211> LENGTH: 63
<212> TYPE: DNA
<213> ORGANISM: Artificial Sequence
<220> FEATURE:
<223> OTHER INFORMATION: part of human CD8A gene

<400> SEQUENCE: 1
atggccttac cagtgaccgc cttgctcctg ccgctggcct tgctgctcca cgccgccagg      60
ccg                                                                    63

<210> SEQ ID NO 2
<211> LENGTH: 135
<212> TYPE: DNA
<213> ORGANISM: Artificial Sequence
<220> FEATURE:
<223> OTHER INFORMATION: part of human CD8A gene sequence

<400> SEQUENCE: 2
accacgacgc cagcgccgcg accaccaaca ccggcgccca ccatcgcgtc gcagcccctg      60
tccctgcgcc cagaggcgtg ccggccagcg gcggggggcg cagtgcacac gagggggctg     120
gacttcgcct gtgat                                                      135

<210> SEQ ID NO 3
<211> LENGTH: 39
<212> TYPE: DNA
<213> ORGANISM: Artificial Sequence
<220> FEATURE:
<223> OTHER INFORMATION: Part of human IgG4 gene sequence

<400> SEQUENCE: 3
```

```
gagtccaaat atggtccccc atgcccatca tgcccagca                                 39
```

<210> SEQ ID NO 4
<211> LENGTH: 204
<212> TYPE: DNA
<213> ORGANISM: Artificial Sequence
<220> FEATURE:
<223> OTHER INFORMATION: part of human CD28 gene sequence

<400> SEQUENCE: 4

```
ttttgggtgc tggtggtggt tggtggagtc ctggcttgct atagcttgct agtaacagtg         60
gcctttatta ttttctgggt gaggagtaag aggagcaggc tcctgcacag tgactacatg        120
aacatgactc cccgccgccc cgggcccacc cgcaagcatt accagcccta tgccccacca        180
cgcgacttcg cagcctatcg ctcc                                               204
```

<210> SEQ ID NO 5
<211> LENGTH: 126
<212> TYPE: DNA
<213> ORGANISM: Artificial Sequence
<220> FEATURE:
<223> OTHER INFORMATION: Part of human 4-1BB gene sequence

<400> SEQUENCE: 5

```
aaacggggca gaaagaaact cctgtatata ttcaaacaac catttatgag accagtacaa         60
actactcaag aggaagatgg ctgtagctgc cgatttccag aagaagaaga aggaggatgt        120
gaactg                                                                  126
```

<210> SEQ ID NO 6
<211> LENGTH: 342
<212> TYPE: DNA
<213> ORGANISM: Artificial Sequence
<220> FEATURE:
<223> OTHER INFORMATION: Part of human CD3zeta gene sequence

<400> SEQUENCE: 6

```
agagtgaagt tcagcaggag cgcagacgcc cccgcgtacc agcagggcca gaaccagctc         60
tataacgagc tcaatctagg acgaagagag gagtacgatg ttttggacaa gagacgtggc        120
cgggaccctg agatgggggg aaagccgcag agaaggaaga accctcagga aggcctgtac        180
aatgaactgc agaaagataa gatggcggag gcctacagtg agattgggat gaaaggcgag        240
cgccggaggg gcaaggggca cgatggcctt taccagggtc tcagtacagc caccaaggac        300
acctacgacg cccttcacat gcaggccctg ccccctcgct aa                          342
```

<210> SEQ ID NO 7
<211> LENGTH: 21
<212> TYPE: PRT
<213> ORGANISM: Artificial Sequence
<220> FEATURE:
<223> OTHER INFORMATION: PART OF HUMAN CD8A PROTEIN SEQUENCE

<400> SEQUENCE: 7

```
Met Ala Leu Pro Val Thr Ala Leu Leu Leu Pro Leu Ala Leu Leu Leu
1               5                   10                  15

His Ala Ala Arg Pro
            20
```

<210> SEQ ID NO 8
<211> LENGTH: 45
<212> TYPE: PRT

```
<213> ORGANISM: Artificial Sequence
<220> FEATURE:
<223> OTHER INFORMATION: part of human CD8A protein sequence

<400> SEQUENCE: 8

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 9
<211> LENGTH: 13
<212> TYPE: PRT
<213> ORGANISM: Artificial Sequence
<220> FEATURE:
<223> OTHER INFORMATION: part of human IgG4 protein sequence

<400> SEQUENCE: 9

Glu Ser Lys Tyr Gly Pro Pro Cys Pro Ser Cys Pro Ala
1               5                   10

<210> SEQ ID NO 10
<211> LENGTH: 68
<212> TYPE: PRT
<213> ORGANISM: Artificial Sequence
<220> FEATURE:
<223> OTHER INFORMATION: part of human CD28 protein sequence

<400> SEQUENCE: 10

Phe Trp Val Leu Val Val Val Gly Gly Val Leu Ala Cys Tyr Ser Leu
1               5                   10                  15

Leu Val Thr Val Ala Phe Ile Ile Phe Trp Val Arg Ser Lys Arg Ser
            20                  25                  30

Arg Leu Leu His Ser Asp Tyr Met Asn Met Thr Pro Arg Arg Pro Gly
        35                  40                  45

Pro Thr Arg Lys His Tyr Gln Pro Tyr Ala Pro Pro Arg Asp Phe Ala
    50                  55                  60

Ala Tyr Arg Ser
65

<210> SEQ ID NO 11
<211> LENGTH: 42
<212> TYPE: PRT
<213> ORGANISM: Artificial Sequence
<220> FEATURE:
<223> OTHER INFORMATION: part of human 4-1BB protein sequence

<400> SEQUENCE: 11

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 12
<211> LENGTH: 113
<212> TYPE: PRT
<213> ORGANISM: Artificial Sequence
<220> FEATURE:
<223> OTHER INFORMATION: part of human CD3zeta sequence
```

<400> SEQUENCE: 12

| Arg | Val | Lys | Phe | Ser | Arg | Ser | Ala | Asp | Ala | Pro | Ala | Tyr | Gln | Gln | Gly |
|---|---|---|---|---|---|---|---|---|---|---|---|---|---|---|---|
| 1 | | | | 5 | | | | | 10 | | | | | 15 | |

| Gln | Asn | Gln | Leu | Tyr | Asn | Glu | Leu | Asn | Leu | Gly | Arg | Arg | Glu | Glu | Tyr |
|---|---|---|---|---|---|---|---|---|---|---|---|---|---|---|---|
| | | | 20 | | | | | 25 | | | | | 30 | | |

| Asp | Val | Leu | Asp | Lys | Arg | Arg | Gly | Arg | Asp | Pro | Glu | Met | Gly | Gly | Lys |
|---|---|---|---|---|---|---|---|---|---|---|---|---|---|---|---|
| | | | 35 | | | | | 40 | | | | | 45 | | |

| Pro | Gln | Arg | Arg | Lys | Asn | Pro | Gln | Glu | Gly | Leu | Tyr | Asn | Glu | Leu | Gln |
|---|---|---|---|---|---|---|---|---|---|---|---|---|---|---|---|
| | 50 | | | | | 55 | | | | | 60 | | | | |

| Lys | Asp | Lys | Met | Ala | Glu | Ala | Tyr | Ser | Glu | Ile | Gly | Met | Lys | Gly | Glu |
|---|---|---|---|---|---|---|---|---|---|---|---|---|---|---|---|
| 65 | | | | 70 | | | | | 75 | | | | | 80 | |

| Arg | Arg | Arg | Gly | Lys | Gly | His | Asp | Gly | Leu | Tyr | Gln | Gly | Leu | Ser | Thr |
|---|---|---|---|---|---|---|---|---|---|---|---|---|---|---|---|
| | | | | 85 | | | | | 90 | | | | | 95 | |

| Ala | Thr | Lys | Asp | Thr | Tyr | Asp | Ala | Leu | His | Met | Gln | Ala | Leu | Pro | Pro |
|---|---|---|---|---|---|---|---|---|---|---|---|---|---|---|---|
| | | | 100 | | | | | 105 | | | | | 110 | | |

Arg

<210> SEQ ID NO 13
<211> LENGTH: 357
<212> TYPE: DNA
<213> ORGANISM: Gallus gallus

<400> SEQUENCE: 13

```
gtccaattgc tggagagcgg tggtggtctg gtgcagccgg gtggctccct gcgtctgagc     60
tgtgcggcga gcggcttccg catcagcgac gaggacatgg gttgggtgcg tcaggcaccg    120
ggcaagggcc tggagtgggt ttctagcatt tacggtccga gcggtagcac ctattacgca    180
gacagcgtga aggtcgtttt acgatcagc cgcgataatt ccaagaacac gttgtatctg    240
caaatgaaca gcctgcgtgc ggaagatacc gcagtttact attgcgcgtc tgcgctggaa    300
ccgctgagcg agccactggg cttctggggt caaggcaccc tggttactgt ctcgagc      357
```

<210> SEQ ID NO 14
<211> LENGTH: 384
<212> TYPE: DNA
<213> ORGANISM: Artificial Sequence
<220> FEATURE:
<223> OTHER INFORMATION: HEN EGG LYSOSYME-HIS fusion

<400> SEQUENCE: 14

```
gtccaattgc tggagagcgg tggtggtctg gtgcagccgg gtggctccct gcgtctgagc     60
tgtgcggcga gcggcttccg catcagcgac gaggacatgg gttgggtgcg tcaggcaccg    120
ggcaagggcc tggagtgggt ttctagcatt tacggtccga gcggtagcac ctattacgca    180
gacagcgtga aggtcgtttt acgatcagc cgcgataatt ccaagaacac gttgtatctg    240
caaatgaaca gcctgcgtgc ggaagatacc gcagtttact attgcgcgtc tgcgctggaa    300
ccgctgagcg agccactggg cttctggggt caaggcaccc tggttactgt ctcgagcgcg    360
gccgcacacc accaccatca ccat                                          384
```

<210> SEQ ID NO 15
<211> LENGTH: 369
<212> TYPE: DNA
<213> ORGANISM: Homo sapiens
<220> FEATURE:
<221> NAME/KEY: VH DOMAIN ANTIBODY BINDING TO PSMA
<222> LOCATION: (1)..(369)

```
<400> SEQUENCE: 15
gaggtgcagc tggtggagtc tgggggaggc gtggtccagc ctgggaggtc cctgagactc    60
tcctgtgcag cctctggatt cccttaatt agctatggca tgcactgggt ccgccaggct    120
ccaggcaagg gctggagtg gtggcattt atgacatatg atggaagtaa tagatactat    180
gcagactccg tgaagggccg attcaccatc tccagagaca attccaagaa cacgctgtat    240
ctgcaaatga acagcctgag agatgaggac acggctctat attactgtgc gagagatcgt    300
atagtgggag gtagggtccc tgatgctttt gatatctggg gccaagggac aatggtcacc    360
gtctcttca                                                            369

<210> SEQ ID NO 16
<211> LENGTH: 339
<212> TYPE: DNA
<213> ORGANISM: Homo sapiens
<220> FEATURE:
<221> NAME/KEY: SINGLE DOMAIN ANTIBODY BINDING TO PSMAvh
<222> LOCATION: (1)..(229)

<400> SEQUENCE: 16
gaggtgcagc tgttggagtc tgggggaggc ttggtacagc ctgggggtc cctgagactc    60 tcctgtgcag cctctggatt cagttttagc agctatgcca tgagttgggt ccgccaggct    120 cagggaagg gctggagtg gtctcaagt attggtgaga atgatggtac cacagactac    180
gcagactccg tgaagggccg attcaccatc tccagagaca attccaagag tatgctgtat    240
ctgcaaatga acagcctgag agtcgaggac acggccgtct attactgtgt gaaagatggt    300
gtccactggg gccagggaac cctggtcacc gtctcctca                           339

<210> SEQ ID NO 17
<211> LENGTH: 381
<212> TYPE: DNA
<213> ORGANISM: Homo sapiens
<220> FEATURE:
<221> NAME/KEY: VH SINGLE DOMAIN ANTIBODY BINDING TO PSMA
<222> LOCATION: (1)..(381)

<400> SEQUENCE: 17
gaggtgcagc tggtggagtc tgggggaggc gtggtccagc ctgggaggtc cctgagactc    60
tcctgtgcag cctctggatt ctccttcagt ggctatggca tgcactgggt ccgccaggct    120
ccaggcaagg gactggagtg gtggcatat atatcatatg atggaagtaa taaatactat    180
gcagactccg tgaagggccg attcaccatc tccagagaca attccaagaa cacgctgtat    240
ctgcaaatga acagcctgag agctgaggac acggctgtgt attactgtgc gaaagatccg    300
gcctggggat acgtttggg ggagtcatcg tcctatgatt ttgatatctg gggccaaggg    360
acaatggtca ctgtctcttc a                                              381

<210> SEQ ID NO 18
<211> LENGTH: 378
<212> TYPE: DNA
<213> ORGANISM: Homo sapiens
<220> FEATURE:
<221> NAME/KEY: VH SINGLE DOMAIN ANTIBODY BINDING TO PSMA
<222> LOCATION: (1)..(378)

<400> SEQUENCE: 18
caggtgcagc tgcaggagtc gggcgcagga ctgttgaagc cttcggagac cctgtccctc    60
acctgcgctg tctatggtgg gtccttcagt gcttacaact ggaactggat ccgccagccc    120
```

```
cccgggaagg ggctggagtg gattggggaa atcaatcata ggggagacac cgcctacaac    180
ccgtccctca agagtcgagt caccatatca gtagacacgt ccaagaatca gttctccctg    240
aacctgacct ctgtgaccgc cgcggacacg gctgtgtatt actgtgcggc acgtggatat    300
agctatggtt ggccccccgg atatatcagt gactcctttg actactgggg ccagggaacc    360
caggtcactg tctcttca                                                  378

<210> SEQ ID NO 19
<211> LENGTH: 357
<212> TYPE: DNA
<213> ORGANISM: Homo sapiens
<220> FEATURE:
<221> NAME/KEY: VH SINGLE DOMAIN ANTIBODY BINDING TO PSMA
<222> LOCATION: (1)..(357)

<400> SEQUENCE: 19
caggtgcagc tacaggagtc gggcccagga ctggtgaagc cttcacagac cctgtccctc     60
acctgcactg tctctggtgg ctccatcagc aatagtggtt attactggag ctgggtccgc    120
cagcacccag ggaaggacct ggagtggatt gggttcatct attacaatgg gagcatccac    180
tacaacccgt ccctcaagag tcgagttatc atatcagtag acacgtctaa gaaccagttc    240
tccctgaaaa tgaactctgt gactgccgcg gacacggccg tgtattactg tgcgagagac    300
ggggatgact acggtgacta cttgaggggc cagggaaccc tggtcaccgt ctcctca       357

<210> SEQ ID NO 20
<211> LENGTH: 117
<212> TYPE: PRT
<213> ORGANISM: Gallus gallus

<400> SEQUENCE: 20

Val Gln Leu Leu Glu Ser Gly Gly Gly Leu Val Gln Pro Gly Gly Ser
1               5                   10                  15

Leu Arg Leu Ser Cys Ala Ala Ser Gly Phe Arg Ile Ser Asp Glu Asp
            20                  25                  30

Met Gly Trp Val Arg Gln Ala Pro Gly Lys Gly Leu Glu Trp Val Ser
        35                  40                  45

Ser Ile Tyr Gly Pro Ser Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ser Ala Leu Glu Pro Leu Ser Glu Pro Leu Gly Phe Trp Gly Gln Gly
            100                 105                 110

Thr Leu Val Thr Val
        115

<210> SEQ ID NO 21
<211> LENGTH: 128
<212> TYPE: PRT
<213> ORGANISM: Artificial Sequence
<220> FEATURE:
<223> OTHER INFORMATION: HEN EGG LYSOZYME-HIS PROTEIN

<400> SEQUENCE: 21

Val Gln Leu Leu Glu Ser Gly Gly Gly Leu Val Gln Pro Gly Gly Ser
1               5                   10                  15

Leu Arg Leu Ser Cys Ala Ala Ser Gly Phe Arg Ile Ser Asp Glu Asp
```

```
                20                  25                  30
Met Gly Trp Val Arg Gln Ala Pro Gly Lys Gly Leu Glu Trp Val Ser
            35                  40                  45

Ser Ile Tyr Gly Pro Ser Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ser Ala Leu Glu Pro Leu Ser Glu Pro Leu Gly Phe Trp Gly Gln Gly
            100                 105                 110

Thr Leu Val Thr Val Ser Ser Ala Ala Ala His His His His His His
        115                 120                 125

<210> SEQ ID NO 22
<211> LENGTH: 123
<212> TYPE: PRT
<213> ORGANISM: Homo sapiens
<220> FEATURE:
<221> NAME/KEY: VH SINGLE DOMAIN ANTIBODY BINDING TO PSMA
<222> LOCATION: (1)..(123)

<400> SEQUENCE: 22

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Pro Leu Ile Ser Tyr
            20                  25                  30

Gly Met His Trp Val Arg Gln Ala Pro Gly Lys Gly Leu Glu Trp Val
        35                  40                  45

Ala Phe Met Thr Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Asp Glu Asp Thr Ala Leu Tyr Tyr Cys
                85                  90                  95

Ala Arg Asp Arg Ile Val Gly Gly Arg Val Pro Asp Ala Phe Asp Ile
            100                 105                 110

Trp Gly Gln Gly Thr Met Val Thr Val Ser Ser
        115                 120

<210> SEQ ID NO 23
<211> LENGTH: 113
<212> TYPE: PRT
<213> ORGANISM: Homo sapiens
<220> FEATURE:
<221> NAME/KEY: VH SINGLE DOMAIN ANTIBODY BINDING TO PSMA
<222> LOCATION: (1)..(113)

<400> SEQUENCE: 23

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Ala Met Ser Trp Val Arg Gln Ala Pro Gly Lys Gly Leu Glu Trp Val
        35                  40                  45

Ser Ser Ile Gly Glu Asn Asp Gly Thr Thr Asp Tyr Ala Asp Ser Val
    50                  55                  60

Lys Gly Arg Phe Thr Ile Ser Arg Asp Asn Ser Lys Ser Met Leu Tyr
```

-continued

```
                65                  70                  75                  80
Leu Gln Met Asn Ser Leu Arg Val Glu Asp Thr Ala Val Tyr Tyr Cys
                    85                  90                  95

Val Lys Asp Gly Val His Trp Gly Gln Gly Thr Leu Val Thr Val Ser
            100                 105                 110

Ser

<210> SEQ ID NO 24
<211> LENGTH: 127
<212> TYPE: PRT
<213> ORGANISM: Homo sapiens
<220> FEATURE:
<221> NAME/KEY: VH SINGLE DOMAIN ANTIBODY BINDING TO PSMA
<222> LOCATION: (1)..(127)

<400> SEQUENCE: 24

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Gly Tyr
                20                  25                  30

Gly Met His Trp Val Arg Gln Ala Pro Gly Lys Gly Leu Glu Trp Val
            35                  40                  45

Ala Tyr Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Lys Asp Pro Ala Trp Gly Leu Arg Leu Gly Glu Ser Ser Ser Tyr
            100                 105                 110

Asp Phe Asp Ile Trp Gly Gln Gly Thr Met Val Thr Val Ser Ser
        115                 120                 125

<210> SEQ ID NO 25
<211> LENGTH: 126
<212> TYPE: PRT
<213> ORGANISM: Homo sapiens
<220> FEATURE:
<221> NAME/KEY: VH SINGLE DOMAIN ANTIBODY BINDING TO PSMA
<222> LOCATION: (1)..(126)

<400> SEQUENCE: 25

Gln Val Gln Leu Gln Glu Ser Gly Ala Gly Leu Leu Lys Pro Ser Glu
1               5                   10                  15

Thr Leu Ser Leu Thr Cys Ala Val Tyr Gly Gly Ser Phe Ser Ala Tyr
                20                  25                  30

Asn Trp Asn Trp Ile Arg Gln Pro Pro Gly Lys Gly Leu Glu Trp Ile
            35                  40                  45

Gly Glu Ile Asn His Arg Gly Asp Thr Ala Tyr Asn Pro Ser Leu Lys
        50                  55                  60

Ser Arg Val Thr Ile Ser Val Asp Thr Ser Lys Asn Gln Phe Ser Leu
65                  70                  75                  80

Asn Leu Thr Ser Val Thr Ala Ala Asp Thr Ala Val Tyr Tyr Cys Ala
                    85                  90                  95

Ala Arg Gly Tyr Ser Tyr Gly Trp Pro Pro Gly Tyr Ile Ser Asp Ser
            100                 105                 110

Phe Asp Tyr Trp Gly Gln Gly Thr Gln Val Thr Val Ser Ser
        115                 120                 125
```

<210> SEQ ID NO 26
<211> LENGTH: 119
<212> TYPE: PRT
<213> ORGANISM: Homo sapiens
<220> FEATURE:
<221> NAME/KEY: VH SINGLE DOMAIN ANTIBODY BINDING TO PSMA
<222> LOCATION: (1)..(119)

<400> SEQUENCE: 26

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Asn Ser
            20                  25                  30

Gly Tyr Tyr Trp Ser Trp Val Arg Gln His Pro Gly Lys Asp Leu Glu
        35                  40                  45

Trp Ile Gly Phe Ile Tyr Tyr Asn Gly Ser Ile His Tyr Asn Pro Ser
    50                  55                  60

Leu Lys Ser Arg Val Ile Ile Ser Val Asp Thr Ser Lys Asn Gln Phe
65                  70                  75                  80

Ser Leu Lys Met Asn Ser Val Thr Ala Ala Asp Thr Ala Val Tyr Tyr
                85                  90                  95

Cys Ala Arg Asp Gly Asp Asp Tyr Gly Asp Tyr Leu Arg Gly Gln Gly
            100                 105                 110

Thr Leu Val Thr Val Ser Ser
        115

<210> SEQ ID NO 27
<211> LENGTH: 70
<212> TYPE: DNA
<213> ORGANISM: Artificial Sequence
<220> FEATURE:
<223> OTHER INFORMATION: PRIMER

<400> SEQUENCE: 27
ggggacaagt ttgtacaaaa aagcaggctt cgaaggagat agaaccatgg ccttaccagt     60
gaccgccttg                                                            70

<210> SEQ ID NO 28
<211> LENGTH: 50
<212> TYPE: DNA
<213> ORGANISM: Artificial Sequence
<220> FEATURE:
<223> OTHER INFORMATION: PRIMER

<400> SEQUENCE: 28
ggggaccact ttgtacaaga aagctgggtt tagcgagggg gcagggcctg               50

<210> SEQ ID NO 29
<211> LENGTH: 14
<212> TYPE: PRT
<213> ORGANISM: Homo sapiens
<220> FEATURE:
<221> NAME/KEY: CDR 3 OF VH SINGLE DOMAIN ANTIBODY BINDING TO PSMA
<222> LOCATION: (1)..(14)

<400> SEQUENCE: 29

Asp Arg Ile Val Gly Gly Arg Val Pro Asp Ala Phe Asp Ile
1               5                   10

<210> SEQ ID NO 30
<211> LENGTH: 4

```
<212> TYPE: PRT
<213> ORGANISM: Homo sapiens
<220> FEATURE:
<221> NAME/KEY: CDR3 OF VH SINGLE DOMAIN ANTIBODY BINDING TO PSMA
<222> LOCATION: (1)..(4)

<400> SEQUENCE: 30

Asp Gly Val His
1

<210> SEQ ID NO 31
<211> LENGTH: 18
<212> TYPE: PRT
<213> ORGANISM: Homo sapiens
<220> FEATURE:
<221> NAME/KEY: CDR3 OF VH SINGLE DOMAIN ANTIBODY BINDING TO PSMA
<222> LOCATION: (1)..(18)

<400> SEQUENCE: 31

Asp Pro Ala Trp Gly Leu Arg Leu Gly Glu Ser Ser Tyr Asp Phe
1               5                   10                  15

Asp Ile

<210> SEQ ID NO 32
<211> LENGTH: 18
<212> TYPE: PRT
<213> ORGANISM: Homo sapiens
<220> FEATURE:
<221> NAME/KEY: CDR3 OF VH SINGLE DOMAIN ANTIBODY BINDING TO PSMA
<222> LOCATION: (1)..(18)

<400> SEQUENCE: 32

Arg Gly Tyr Ser Tyr Gly Trp Pro Pro Gly Tyr Ile Ser Asp Ser Phe
1               5                   10                  15

Asp Tyr

<210> SEQ ID NO 33
<211> LENGTH: 8
<212> TYPE: PRT
<213> ORGANISM: Homo sapiens
<220> FEATURE:
<221> NAME/KEY: CDR3 OF VH SINGLE DOMAIN ANTIBODY BINDING TO PSMA
<222> LOCATION: (1)..(8)

<400> SEQUENCE: 33

Asp Gly Asp Asp Tyr Gly Asp Tyr
1               5

<210> SEQ ID NO 34
<211> LENGTH: 749
<212> TYPE: PRT
<213> ORGANISM: Homo sapiens
<220> FEATURE:
<221> NAME/KEY: HUMAN PSMA PROTEIN
<222> LOCATION: (1)..(749)

<400> SEQUENCE: 34

Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
                20                  25                  30

Phe Leu Leu Gly Phe Leu Phe Gly Trp Phe Ile Lys Ser Ser Asn Glu
            35                  40                  45

Ala Thr Asn Ile Thr Pro Lys His Asn Met Lys Ala Phe Leu Asp Glu
        50                  55                  60
```

```
Leu Lys Ala Glu Asn Ile Lys Lys Phe Leu Tyr Asn Phe Thr Gln Ile
 65                  70                  75                  80

Pro His Leu Ala Gly Thr Glu Gln Asn Phe Gln Leu Ala Lys Gln Ile
                 85                  90                  95

Gln Ser Gln Trp Lys Glu Phe Gly Leu Asp Ser Val Glu Leu Ala His
            100                 105                 110

Tyr Asp Val Leu Leu Ser Tyr Pro Asn Lys Thr His Pro Asn Tyr Ile
        115                 120                 125

Ser Ile Ile Asn Glu Asp Gly Asn Glu Ile Phe Asn Thr Ser Leu Phe
    130                 135                 140

Glu Pro Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
            180                 185                 190

Lys Ile Asn Cys Ser Gly Lys Ile Val Ile Ala Arg Tyr Gly Lys Val
        195                 200                 205

Phe Arg Gly Asn Lys Val Lys Asn Ala Gln Leu Ala Gly Ala Lys Gly
    210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Gly Val Gln Arg Gly
                245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg Arg Gly Ile Ala Glu Ala Val Gly
        275                 280                 285

Leu Pro Ser Ile Pro Val His Pro Ile Gly Tyr Asp Ala Gln Lys Leu
    290                 295                 300

Leu Glu Lys Met Gly Gly Ser Ala Pro Pro Asp Ser Ser Trp Arg Gly
305                 310                 315                 320

Ser Leu Lys Val Pro Tyr Asn Val Gly Pro Gly Phe Thr Gly Asn Phe
                325                 330                 335

Ser Thr Gln Lys Val Lys Met His Ile His Ser Thr Asn Glu Val Thr
            340                 345                 350

Arg Ile Tyr Asn Val Ile Gly Thr Leu Arg Gly Ala Val Glu Pro Asp
        355                 360                 365

Arg Tyr Val Ile Leu Gly Gly His Arg Asp Ser Trp Val Phe Gly Gly
    370                 375                 380

Ile Asp Pro Gln Ser Gly Ala Ala Val Val His Glu Ile Val Arg Ser
385                 390                 395                 400

Phe Gly Thr Leu Lys Lys Glu Gly Trp Arg Pro Arg Arg Thr Ile Leu
                405                 410                 415

Phe Ala Ser Trp Asp Ala Glu Glu Phe Gly Leu Leu Gly Ser Thr Glu
            420                 425                 430

Trp Ala Glu Glu Asn Ser Arg Leu Leu Gln Glu Arg Gly Val Ala Tyr
        435                 440                 445

Ile Asn Ala Asp Ser Ser Ile Glu Gly Asn Tyr Thr Leu Arg Val Asp
    450                 455                 460

Cys Thr Pro Leu Met Tyr Ser Leu Val His Asn Leu Thr Lys Glu Leu
465                 470                 475                 480
```

```
Lys Ser Pro Asp Glu Gly Phe Glu Gly Lys Ser Leu Tyr Glu Ser Trp
                485             490                 495

Thr Lys Lys Ser Pro Ser Pro Glu Phe Ser Gly Met Pro Arg Ile Ser
            500             505                 510

Lys Leu Gly Ser Gly Asn Asp Phe Glu Val Phe Phe Gln Arg Leu Gly
            515             520                 525

Ile Ala Ser Gly Arg Ala Arg Tyr Thr Lys Asn Trp Glu Thr Asn Lys
            530             535             540

Phe Ser Gly Tyr Pro Leu Tyr His Ser Val Tyr Glu Thr Tyr Glu Leu
545                 550             555                 560

Val Glu Lys Phe Tyr Asp Pro Met Phe Lys Tyr His Leu Thr Val Ala
                565             570                 575

Gln Val Arg Gly Gly Met Val Phe Glu Leu Ala Asn Ser Ile Val Leu
            580             585                 590

Pro Phe Asp Cys Arg Asp Tyr Ala Val Val Leu Arg Lys Tyr Ala Asp
            595             600             605

Lys Ile Tyr Ser Ile Ser Met Lys His Pro Gln Glu Met Lys Thr Tyr
    610             615             620

Ser Val Ser Phe Asp Ser Leu Phe Ser Ala Val Lys Asn Phe Thr Glu
625             630             635                 640

Ile Ala Ser Lys Phe Ser Glu Arg Leu Gln Asp Phe Asp Lys Ser Asn
                645             650             655

Pro Ile Val Leu Arg Met Met Asn Asp Gln Leu Met Phe Leu Glu Arg
            660             665             670

Ala Phe Ile Asp Pro Leu Gly Leu Pro Asp Arg Pro Phe Tyr Arg His
            675             680             685

Val Ile Tyr Ala Pro Ser Ser His Asn Lys Tyr Ala Gly Glu Ser Phe
    690             695             700

Pro Gly Ile Tyr Asp Ala Leu Phe Asp Ile Glu Ser Lys Val Asp Pro
705             710             715                 720

Ser Lys Ala Trp Gly Glu Val Lys Arg Gln Ile Tyr Val Ala Ala Phe
                725             730                 735

Thr Val Gln Ala Ala Ala Glu Thr Leu Ser Glu Val Ala
                740             745
```

CHIMERIC ANTIGEN RECEPTOR WITH SINGLE DOMAIN ANTIBODY

CROSS REFERENCE TO RELATED APPLICATIONS

This application is a § 371 national phase application of PCT Application No. PCT/GB2017/051272, filed on May 8, 2017, which claims priority to British Application No. 1607968.3 filed on May 6, 2016, the entire contents of each of which is incorporated by reference herein.

STATEMENT REGARDING ELECTRONIC FILING OF A SEQUENCE LISTING

A Sequence Listing in ASCII text format, submitted under 37 C.F.R. § 1.821, entitled 1553.5_ST25.txt, 26,865 bytes in size, generated on Nov. 5, 2018 and filed via EFS-Web, is provided in lieu of a paper copy. This Sequence Listing is hereby incorporated herein by reference into the specification for its disclosures.

FIELD OF THE INVENTION

The present invention relates to chimeric antigen receptors (CARs) comprising one or more single domain antibody wherein the domain is a human variable heavy chain ($V_H$) domain, in particular for the treatment of prostate cancer. CARs are able to redirect immune cell specificity and reactivity toward a selected target exploiting the ligand-binding domain properties. The present invention also relates to a CAR comprising multiple human single $V_H$ domain antibodies.

The present invention further relates to polynucleotides encoding a CAR of the invention, vectors encoding such polypeptides and isolated cells expressing the CAR of the invention at their surface. Such cells can be used in therapy, in particular for the treatment of cancer. Methods for treating disease, for example cancer, are also within the scope of the invention.

INTRODUCTION

Adoptive cellular therapy (ACT) has received much attention as a technique for cancer treatment. One therapeutic approach of ACT involves genetic engineering of T cells to express chimeric antigen receptors (CARs) on the surface of T cells to enable targeting of specific tumours. Once the CAR is expressed in T cells, the CAR modified T cell (CAR-T or CAR-T cell) acquires properties that include antigen-specific recognition, activation and proliferation and the cells thus act as "living drugs". The purpose of expressing a CAR in a T cell is therefore to redirect immune reactivity of the cell to a chosen target. Furthermore, CARs with different strength and signalling can also modulate T cell expansion as well as after the strength of T cell activation.

CARs are synthetic receptors typically consisting of a targeting/binding moiety that is associated with one or more signaling domains in a single fusion molecule. The binding moiety of a CAR typically consists of an antigen-binding domain of a single-chain antibody (scFv) comprising the light and heavy chain variable fragments of a monoclonal antibody joined by a flexible linker. The scFv retains the same specificity and a similar affinity as the full antibody from which it was derived and is capable to binding to the specific target of interest.

CARs combine antigen-specificity and T cell activating properties in a single fusion molecule. First generation CARs typically included the cytoplasmic region of the CD3zeta or Fc receptor γ chain as their signalling domain. First generation CARs have been tested in phase I clinical studies in patients with ovarian cancer, renal cancer, lymphoma, and neuroblastoma, where they have induced modest responses (reviewed in Sadelain et al., Curr Opin Immunol, 21 (2): 215-223, 2009). Second generation CARs, which contain the signalling domains of both CD28 and CD3zeta, provide dual signalling to direct combined activating and co-stimulatory signals. Third generation CARs are more complex with three or more signalling domains (reviewed in Sadelain et al., Cancer Discovery (3), 388-398, 2013 and Dotti et al. Immuno. Rev, 257 (1), 1-36, 2014).

Prostate cancer is the most commonly diagnosed non-skin-related malignancy in males in developed countries. It is estimated that one in six males will be diagnosed with prostate cancer. Current treatments for prostate cancer include surgery, radiation, and adjuvant hormonal therapy. Although these therapies are relatively effective in the early stages of disease, the majority of patients initially diagnosed with localized prostate cancer ultimately relapse. Whilst chemotherapy is one of the most widely used approaches in combating advanced prostate cancer, its therapeutic efficacy is usually insufficient due to lack of specificity and associated toxicity. Lack of targeted delivery to prostate cancer cells is one of the primary obstacles in achieving feasible therapeutic effect. Consequently, there remains a critical need for strategies to increase the selectivity of anti-prostate cancer agents (Barve et al., J Control Release. 2014 Aug. 10; 0: 118-132).

The diagnosis of prostate cancer has greatly improved following the use of serum-based markers such as the prostate specific antigen (PSA). In addition, prostate tumour-associated antigens offer targets for tumour imaging, diagnosis, and targeted therapies. The prostate specific membrane antigen (PSMA), a prostate tumour associated marker, is such a target. PSMA-specific CAR-Ts using a scFv based binding moiety have been generated for use in the treatment of prostate cancer (Zuccolotto et al., PLOS One (9), e109427 2014).

When a CAR construct is expressed on the surface of a T cell and binds its target protein, T cell activation is triggered. T cell activation is a powerful weapon and non-specific activation of T cells is therefore a major safety concern. scFv are typically used as targeting agents, but they have a number of characteristics that can have a negative impact on the therapeutic efficacy of CAR-Ts. scFv are characterised by poor expression and stability, prone to unfolding and aggregation. As a result, they often make it challenging to achieve CAR expression or are non-specific for targeting of T cells and non-specific for the initiation of signalling. CAR-Ts that have scFv can also form clusters on the membrane due to crosslinking of heavy and light chains of different CAR-Ts. This results in unwanted constitutive signalling.

Furthermore, scFv used in CAR-Ts are also usually derived from mouse mAbs and thus have potential immunogenicity issues as the anti-scFv response not only initiates T cell response by potentially crosslinking but also eradicates CAR-Ts from circulation.

Without wishing to be bound by theory, these problems are likely to be compounded when scFvs are used to design CAR-Ts having bispecific, bivalent or biparatopic antigen binding moieties.

Whilst scFv typically used in CARs have the potential for unwanted aggregation, cluster formation and immunogenicity, the use of human $V_H$ domains provides a stable format with substantially reduced potential for immunogenicity, aggregation or unfolding. This is particularly useful when designing CAR-Ts having bispecific, bivalent or biparatopic antigen binding moieties. As demonstrated by the inventors herein, multiple human $V_H$ domains can readily be used in such mutimeric format thus facilitating the generation of multispecific CARs that enable simultaneous targeting of more than one target or epitope.

Therefore, the present invention is aimed at mitigating the shortcomings of existing CAR-T therapies by providing CARs and CAR-Ts with a single $V_H$ domain antibody, in particular with multiple single human $V_H$ domain antibodies.

SUMMARY OF THE INVENTION

The invention relates to the use of human, preferably multiple human $V_H$ domains as building blocks to make CARs and CAR-Ts with advantageous antigen binding domains. A $V_H$ domain is also termed Humabody® herein. The term $V_H$ domain as used herein refers to a single human $V_H$ domain antibody ($V_H$ sdAb). These terms are thus used interchangeably.

$V_H$ domains are small molecules of 12-14 kDa which can be combined into different formats (formatted Humabody®) to give multivalent or multispecific antigen binding domains of a CAR. $V_H$ domains are robust and are characterised by high affinity and stability in serum.

The CAR constructs described herein include a human $V_H$ domain (preferably multiple $V_H$ domains) that recognises a target protein of interest, e.g. a protein expressed on a tumour cell, such as an antigen.

Thus, in a first aspect, the invention relates to an isolated CAR comprising an antigen binding domain, a transmembrane domain and an intracellular signalling domain wherein said antigen binding domain comprises one or more, for example at least two, human variable heavy chain ($V_H$) domains and is devoid of light chains.

In a second aspect, the invention relates to an isolated nucleic acid encoding a CAR according to the invention.

In a third aspect, the invention relates to a vector comprising a nucleic acid of the invention. In another aspect, the invention relates to a host cell comprising a nucleic acid or vector of the invention.

In another aspect, the invention relates to an isolated cell or cell population comprising one or more CAR of the invention. Such cell has been genetically modified to express a CAR of the invention. In one embodiment, the cell is a T cell (CAR-T).

In another aspect, the invention relates to a pharmaceutical composition comprising an isolated cell, for example a T cell, comprising one or more CAR of the invention (e.g. a CAR-T) and a pharmaceutical acceptable carrier, excipient or diluent.

In another aspect, the invention relates to a method for treating cancer comprising administering a T cell or pharmaceutical composition of the invention.

In another aspect, the invention relates to an isolated cell or cell population of the invention for use in therapy. In another aspect, the invention relates to a cell of the invention for use in the treatment of cancer.

In another aspect, the invention relates to the use of an isolated cell or cell population of the invention in the manufacture of a medicament for the treatment of cancer.

In another aspect, the invention relates to a method for stimulating a T cell-mediated immune response to a target cell population or tissue in a subject, the method comprising administering to a subject an effective amount of a cell expressing a CAR of the invention, wherein the antigen binding domain is selected to specifically recognize the target cell population or tissue.

In another aspect, the invention relates to a method of providing an anti-tumour immunity in a subject, the method comprising administering to the mammal an effective amount of a cell genetically modified to express a CAR of the invention.

In another aspect, the invention relates to a method, for example an ex vivo method, for generating a cell or cell population for use in adaptive immunotherapy comprising transforming said cell or cell population with a CAR of the invention.

In another aspect, the invention relates to a pharmaceutical composition comprising a cell or cell population of the invention.

In another aspect, the invention relates to a kit comprising a pharmaceutical composition, cell or cell population of the invention.

FIGURES

The invention is further described in the following non-limiting figures.

FIG. 1 This shows the general structure of a $3^{rd}$ generation CAR-T using scFv comprising $V_H$ and $V_L$ domains.

Figure 2:
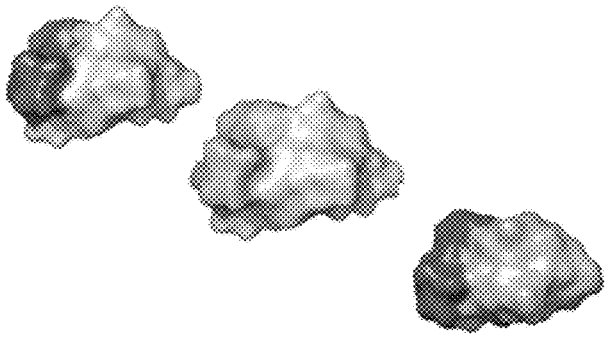
Figure 2:
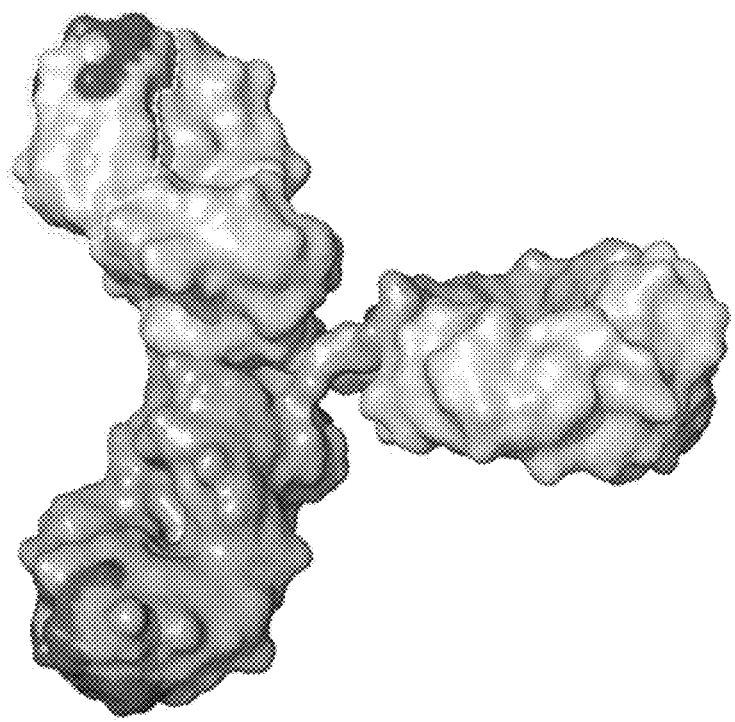

FIG. 2 Full antibody compared to $V_H$.

FIG. 3 Structure of a CAR-T according to the invention. In a) and b), the CAR-T comprises two $V_H$ domains with each $V_H$ domain binding to a different epitope. c). CAR-T with specificity for two different target antigens.

Figure 4:
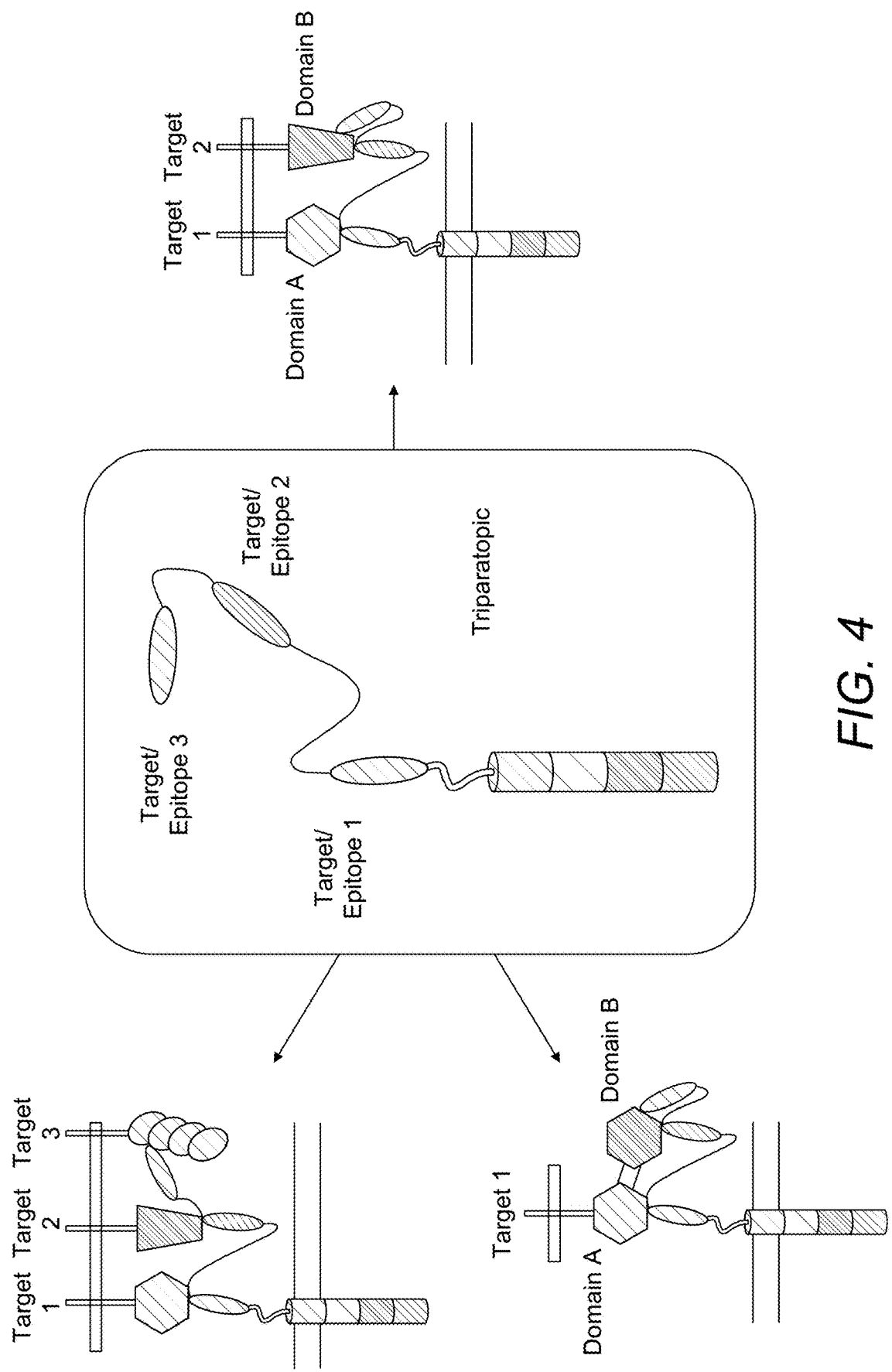

FIG. 4 Binding mechanisms of a CAR-T according to the invention.

Figure 5A:
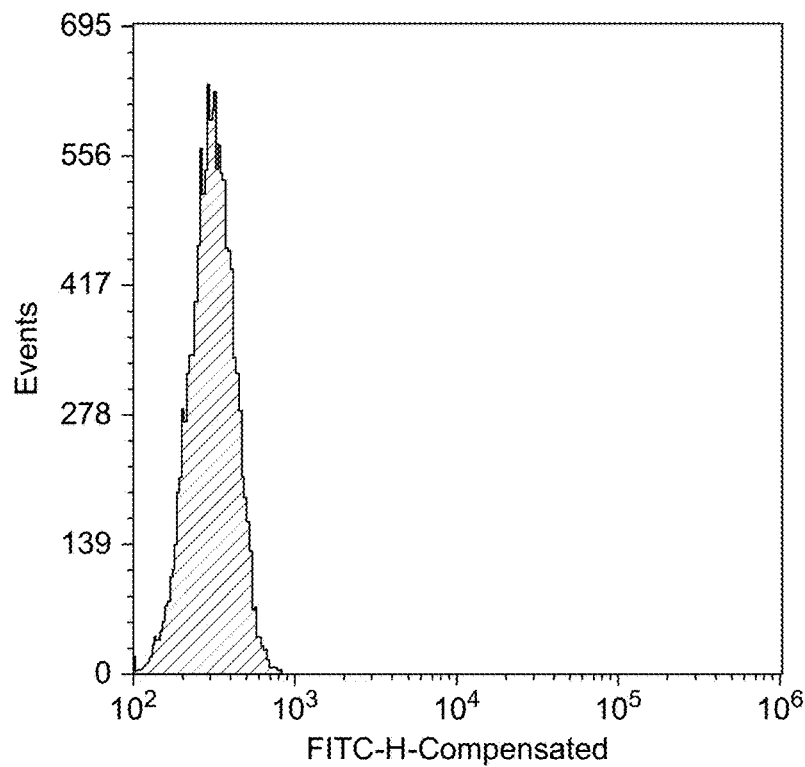
Figure 5B:
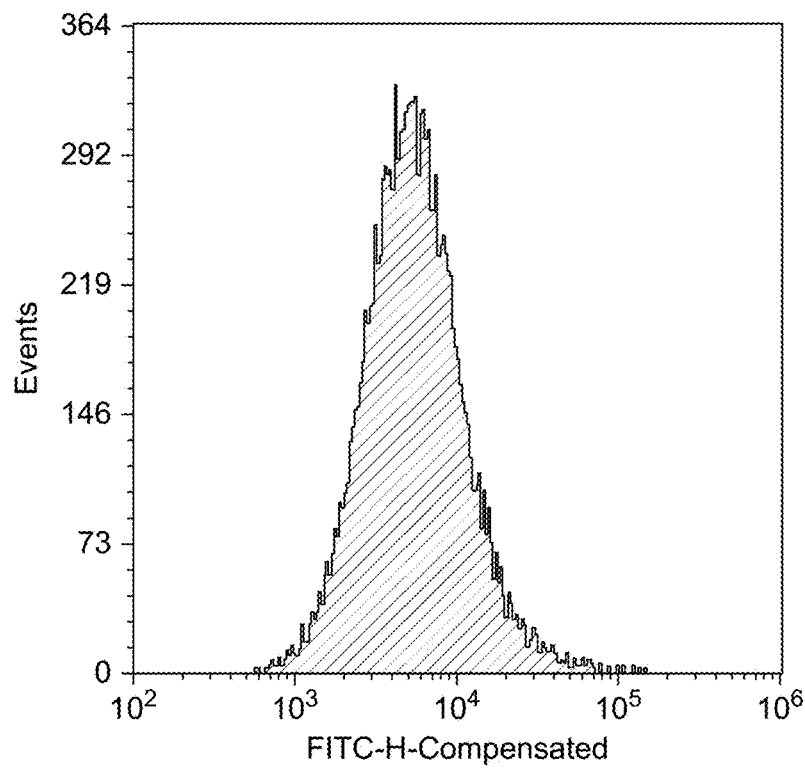

FIG. 5 CAR-T expression in cells. GFP expression in cells transduced with GFP lentivirus. Transduction with GFP lentivirus results in a marked shift to the right, indicating expression of the fluorescent protein within the JurkatE6.1 cells. A. JurkatE6.1 cells. B. JurkatE6.1 cells transduced with GFP lentivirus.

Figure 6A:
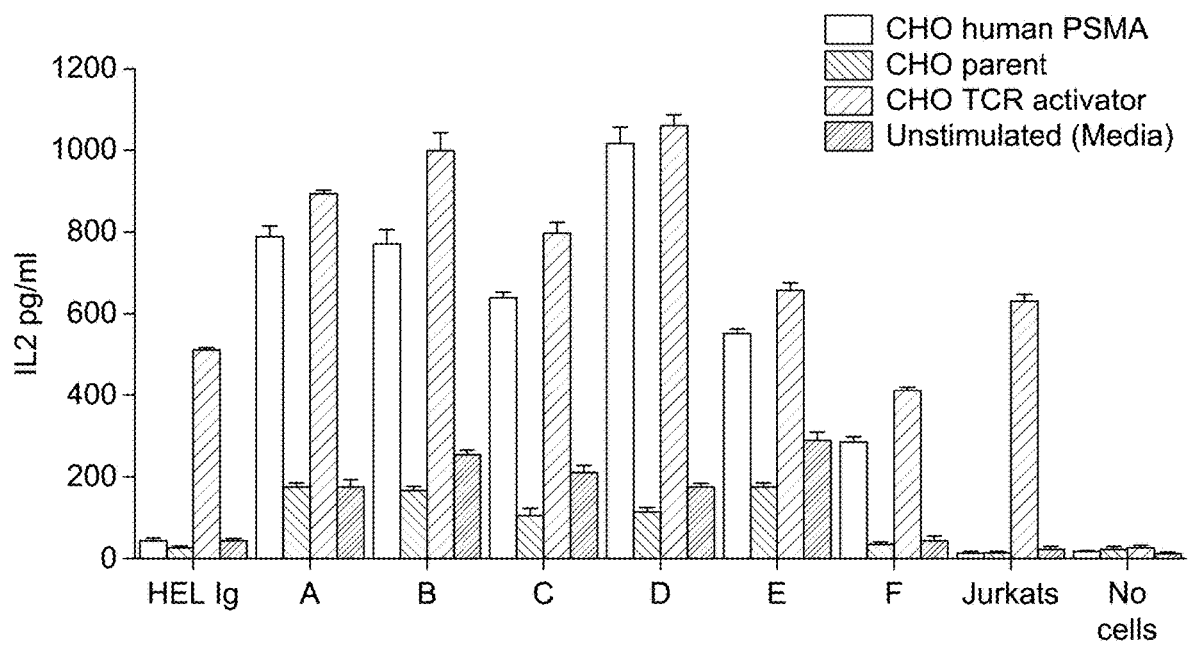
Figure 6B:
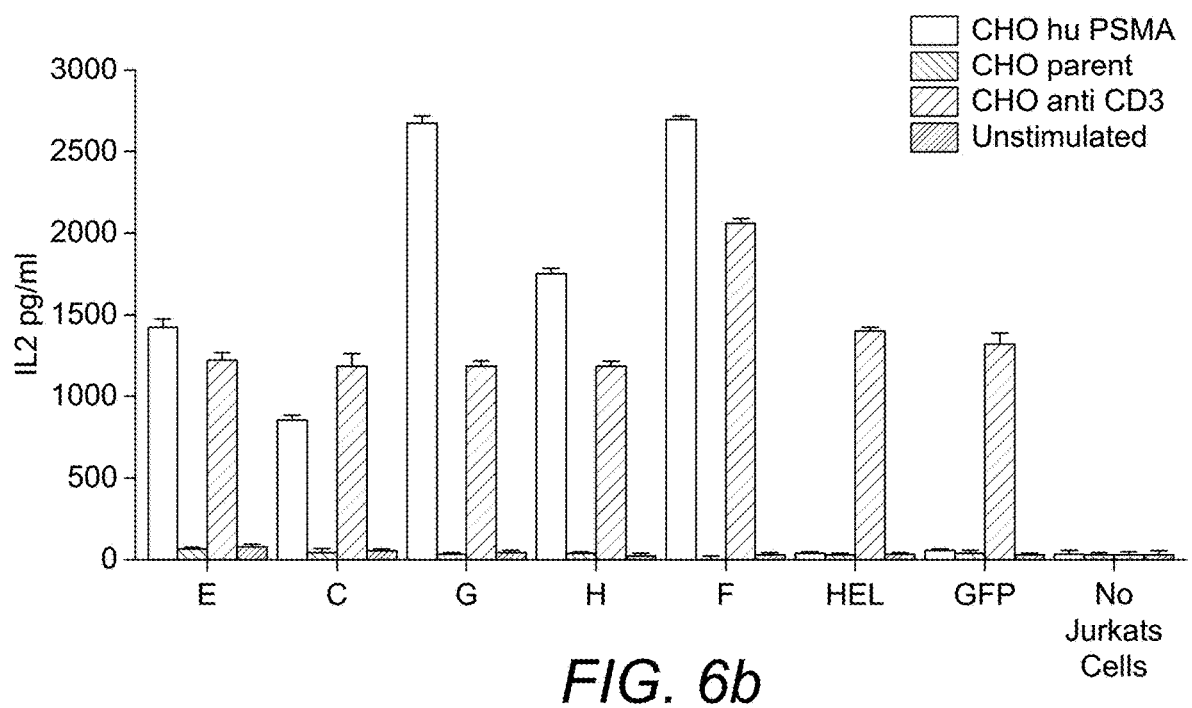

FIG. 6. CAR-T expression in cells demonstrates upregulation of IL2 levels in response to stimulation by specific antigen binding. FIG. 6a. A=HB1-8a, B=HB1-Ig, C=HB2-Ig, D=HB3-8a, E=HB3-Ig, F=prostate specific antigen (PSMA) binding antibody fragment (positive control construct in single chain format). FIG. 6b. C, E and F as above. G=HB4-Ig, H=HB5-Ig, FIG. 7. Expression of formatted VH CAR constructs in cells demonstrates upregulation of IL2 levels in response to stimulation by specific antigen binding. I=HB3-Ig-HB3-Ig; J=HB2-Ig-HB3-Ig; K=HB3-Ig-MSA (murine serum albumin)

DETAILED DESCRIPTION

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Generally, nomenclatures used in connection with, and techniques of, cell and tissue culture, pathology, oncology, molecular biology, immunology, microbiology, genetics and protein and nucleic acid chemistry and hybridization described herein are those well-known and commonly used in the art. The methods and techniques of the present disclosure are generally performed according to conventional methods well-known in the art and as described in various general and more specific references that are cited and discussed throughout the present specification unless otherwise indicated. See, e.g., Sambrook et al., Molecular Cloning: A Laboratory Manual (4th ed., Cold Spring Harbor Laboratory Press, Cold Spring Harbor, N.Y. (2013)). Enzymatic reactions and purification techniques are performed according to manufacturer's specifications, as commonly accomplished in the art or as described herein. The nomenclatures used in connection with, and the laboratory procedures and techniques of, immunology, molecular biology, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

The invention relates to the use of human $V_H$ domains, preferably multiple human $V_H$ domains, as building blocks to make CARs with advantageous antigen binding domains.

The terms "Chimeric antigen receptor" or "CAR" or "CARs" as used herein refer to engineered receptors, which graft an antigen specificity onto cells (for example T cells such as naive T cells, central memory T cells, effector memory T cells or combination thereof) thus combining the antigen binding properties of the antigen binding domain with the lytic capacity and self renewal of T cells. CARs are also known as artificial T cell receptors, chimeric T cell receptors or chimeric immunoreceptors. The term "antigen binding domain or "antigen-specific targeting domain" as used herein refers to the region of the CAR which targets and binds to specific antigens. When a CAR is expressed in a host cell, this domain forms the extracellular domain (ectodomain).

The CAR of the invention comprises a molecule of the general formula:

human $V_H$ sdAb(n)-transmembrane domain-Intracellular signaling domain wherein n is 1 or more. In one embodiment, n is at least 2, for example 2, 3, 4 or 5. The human $V_H$ domain forms the antigen binding domain and is located at the extracellular side when expressed in a cell.

The term "antibody", broadly refers to any immunoglobulin (Ig) molecule, or antigen binding portion thereof, comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art. In a full-length antibody, each heavy chain is comprised of a heavy chain variable region (abbreviated herein as HCVR or $V_H$) and a heavy chain constant region. The heavy chain constant region is comprised of three domains, $C_H1$, $C_H2$ and $C_H3$. Each light chain is comprised of a light chain variable region (abbreviated herein as LCVR or $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG 1, IgG2, IgG 3, IgG4, IgAI and IgA2) or subclass.

An antibody fragment is a portion of an antibody, for example as F(ab')2, Fab, Fv, sFv and the like. Functional fragments of a full length antibody retain the target specificity of a full length antibody. Recombinant functional antibody fragments, such as Fab (Fragment, antibody), scFv (single chain variable chain fragments) and single domain antibodies (dAbs) have therefore been used to develop therapeutics as an alternative to therapeutics based on mAbs. scFv fragments (~25 kDa) consist of the two variable domains, $V_H$ and $V_L$. Naturally, $V_H$ and $V_L$ domains are non-covalently associated via hydrophobic interaction and tend to dissociate. However, stable fragments can be engineered by linking the domains with a hydrophilic flexible linker to create a single chain Fv (scFv). The smallest antigen binding fragment is the single variable fragment, namely the $V_H$ or $V_L$ domain. Binding to a light chain/heavy chain partner respectively is not required for target binding. Such fragments are used in single domain antibodies. A single domain antibody (~12 to 15 kDa) therefore has either the $V_H$ or $V_L$ domain.

The terms "single domain antibody, variable single domain or immunoglobulin single variable domain (ISV)" are all well known in the art and describe the single variable fragment of an antibody that binds to a target antigen. These terms are used interchangeably herein. As explained below, preferred embodiments of the various aspects of the invention relate to CARs comprising single heavy chain variable domain antibodies/immunoglobulin heavy chain single variable domains which bind a PSMA antigen in the absence of light chain. Human heavy chain single variable domain antibodies are particularly preferred. Such binding molecules are also termed Humabody® herein. Humabody® is a registered trademark of Crescendo Biologics Ltd.

Thus, in some preferred embodiments, the CARs of the invention comprise a binding domain that comprises or consist of a single domain antibody wherein said domain is a human heavy chain variable domain. Thus, in a preferred aspect, the CARs of the invention comprise one or more binding domain that is devoid of $V_L$ domains.

Each single $V_H$ domain antibody comprises three CDRs and four FRs, arranged from amino-terminus to carboxy-terminus in the following order: FR1-CDR1-FR2-CDR2-FR3-CDR3-FR4. Thus, in one embodiment of the invention, the domain is a human variable heavy chain ($V_H$) domain with the following formula FR1-CDR1-FR2-CDR2-FR3-CDR3-FR4.

The term "CDR" refers to the complementarity-determining region within antibody variable sequences. There are three CDRs in each of the variable regions of the heavy chain and the light chain, which are designated CDR1, CDR2 and CDR3, for each of the variable regions. The term "CDR set" refers to a group of three CDRs that occur in a single variable region capable of binding the antigen. The exact boundaries of these CDRs have been defined differently according to different systems. The system described by Kabat is used herein. The terms "Kabat numbering", "Kabat definitions" and "Kabat labeling" are used interchangeably herein. These terms, which are recognized in the art, refer to a system of numbering amino acid residues which are more variable (i.e., hypervariable) than other amino acid residues in the heavy and light chain variable regions of an antibody, or an antigen binding portion thereof (Kabat et al., (1971) Ann. NY Acad. Sci. 190:382-391 and Kabat, et al., (1991) Sequences of Proteins of Immunological Interest, Fifth Edition, U.S. Department of Health and Human Services, NIH Publication No. 91-3242).

As used herein, the $V_H$ domain is a human $V_H$ domain. The term "a human $V_H$ domain" includes a $V_H$ domain that is derived from or based on a human $V_H$ domain amino acid or nucleic acid sequence. Thus, the term includes variable heavy chain regions derived from human germline immunoglobulin sequences. As used herein, the term human $V_H$ domain includes $V_H$ domains that are isolated from transgenic mice expressing human immunoglobulin V genes, in particular in response to an immunisation with an antigen of interest, for example as described in WO 2016/062990. Such domains are preferably fully human. In one embodiment, a human $V_H$ domain can also include a $V_H$ domain that is derived from or based on a human $V_H$ domain amino acid or nucleic acid sequence encoding such $V_H$ domain. Thus, the term includes variable heavy chain regions derived from or encoded by human germline immunoglobulin sequences. A substantially human $V_H$ domain or $V_H$ domain that is derived from or based on a human $V_H$ domain may include amino acid residues not encoded by human germline immunoglobulin sequences (e.g., mutations introduced in vitro, e.g. by random or site-specific mutagenesis, or introduced by somatic mutation in vivo). The term "human $V_H$ domain" therefore also includes a substantially human $V_H$ domain wherein one or more amino acid residue has been modified. For example, a substantially human $V_H$ domain the $V_H$ domain may include up to 10, for example 1, 2, 3, 4 or 5 amino acid modifications compared to a fully human sequence.

However, the term "human $V_H$ domain" or "substantially human $V_H$ domain", as used herein, is not intended to include antibodies in which CDR sequences derived from the germline of another mammalian species, such as a mouse, have been grafted onto human framework sequences. Preferably, the term "human $V_H$ domain", as used herein, is also not intended to include camelized $V_H$ domains, that is human $V_H$ domains that have been specifically modified, for example in vitro by conventional mutagenesis methods to select predetermined positions in the $V_H$ domains sequence and introduce one or more point mutation at the predetermined position to change one or more predetermined residue to a specific residue that can be found in a camelid $V_{HH}$ domain.

As used herein, the term $V_H$ or "variable domain" refers to immunoglobulin variable domains defined by Kabat et al., Sequences of Immunological Interest, $5^{th}$ ed., U.S. Dept. Health & Human Services, Washington, D.C. (1991). The numbering and positioning of CDR amino acid residues within the variable domains is in accordance with the well-known Kabat numbering convention.

The antigen binding domain used in a CAR of the invention thus comprises one, preferably more than one $V_H$ domain, i.e. one or more $V_H$ single domain antibody, and is devoid of light chains. In a preferred embodiment, the antigen binding domain comprises at least two $V_H$ single domain antibodies.

As explained in detail below, a CAR of the invention preferably comprises at least two antigen binding domains (each comprising a $V_H$ single domain antibody) which target one or more antigen.

In one embodiment, the antigen binding domain of a CAR of the invention comprises two or at least two $V_H$ domains that are specific for the same antigen, thus providing a bivalent binding molecule. In one embodiment, the antigen binding domain comprises two or at least two $V_H$ single domain antibodies that are specific for the same antigen, but bind to different epitopes on said antigen. In other words, the antigen binding domain comprises a first $V_H$ single domain antibody that binds to a first epitope and a second $V_H$ single domain antibody that binds to a second epitope. The epitopes may be overlapping. Thus, the antigen binding domain is biparatopic and the scope of the invention includes a biparatopic CAR. In yet another embodiment, the antigen binding domain comprises two $V_H$ domains that are specific for the same antigen and bind to the same epitopes on said antigen.

In another embodiment, the antigen binding domain comprises two single $V_H$ domain antibodies that are specific for two different antigens, thus providing a bispecific antigen binding domain. In other words, the antigen binding domain comprises a first $V_H$ single domain antibody that binds to a first target and a second $V_H$ single domain antibody that binds to a second target. Thus, in certain embodiments, the invention relates to bispecific CARs.

As used herein, the term "bispecific CAR" or "bispecifc antigen binding domain" thus refers to a polypeptide that comprises a binding molecule as described herein which has a binding site that has binding specificity for a first target antigen, and a second polypeptide domain which has a binding site that has binding specificity for a second antigen target, i.e., the bispecific binding molecule has specificity for two targets. The first target and the second target are not the same, i.e. are different targets, e.g., proteins; both may be present on a cell surface. Accordingly, a bispecific binding molecule as described herein can selectively and specifically bind to a cell that expresses (or displays on its cell surface) the first target and the second target. In another embodiment, the binding molecule comprises more than two antigen-binding domains providing a multispecific binding molecule. A multispecific antigen-binding domain as described herein can in addition to binding a first target bind one or more additional targets, i.e., a multispecific polypeptide can bind at least two, at least three, at least four, at least five, at least six, or more targets, wherein the multispecific polypeptide agent has at least two, at least, at least three, at least four, at least five, at least six, or more target binding sites respectively.

Antigen binding domains that comprise three or more single $V_H$ domain antibodies are therefore also within the scope of the invention.

Two or more $V_H$ may be connected by a linker, for example a polypeptide linker. Suitable linkers, for example comprising linker include GS residues such as $(Gly_4Ser)_n$, where n=from 1 to 10, e.g., 1, 2, 3, 4, 5, 6, 7, 8, 9 or 10.

The one or more single $V_H$ domain antibody which forms the antigen binding unit of the CAR of the invention, "binds" or is "capable of binding" an antigen of interest, i.e. targets, antigen with sufficient affinity such the CAR is useful in therapy in targeting a cell or tissue expressing the antigen.

As used herein, the term "target" refers to a biological molecule (e.g., antigen, peptide, polypeptide, protein, lipid, carbohydrate) to which a polypeptide domain which has a binding site can selectively bind. The target can be, for example, an intracellular target (such as an intracellular protein target) or a cell-surface target (such as a membrane protein, e.g., a receptor protein). Preferably, a target is a cell-surface target, such as a cell-surface protein.

In one embodiment, the target of the antigen binding domain of the CAR is a tumor antigen. In one embodiment, the tumor antigen is associated with a hematologic malignancy. In another embodiment, the tumor antigen is associated with a solid tumor. In yet another embodiment, the tumor antigen is selected from the group consisting of PSMA, PSCA, BCMA, CS1, GPC3, CSPG4, EGFR, CD123, 5T4, CD23, L1CAM, MUC16, ROR1, SLAMF7, cKit, CD19, CD20, CD22, CD33, CD38, CD53, CD92, CD100, CD148, CD150, CD200, CD261, CD262, CD362, ROR1, mesothelin, CD33/IL3Ra, c-Met, Glycolipid F77, EGFRvIII, GD-2, NY-ESO-1 TCR or MAGE A3 TCR, human telomerase reverse transcriptase (hTERT), survivin, cytochrome P450 1B1 (CY1B), HER2, Wilm's tumor gene 1 (WT1), livin, alphafetoprotein (AFP), carcinoembryonic antigen (CEA), mucin 16. MUC1, p53, cyclin, an immuno checkpoint target or combinations thereof. However, a skilled person would understand that other tumor antigens are also targets within the scope of the invention.

In one embodiment, the $V_H$ domain binds PSMA, preferably to wild type human PSMA (accession NO. Q04609). The sequence for the wild type human PSMA monomer is shown below (SEQ ID NO. 34).

```
  1 MWNLLHETDS AVATARRPRW LCAGALVLAG GFFLLGFLFG
    WFIKSSNEAT NITPKHNMKA

61 FLDELKAENI KKFLYNFTQI PHLAGTEQNF QLAKQIQSQW
    KEFGLDSVEL AHYDVLLSYP

121 NKTHPNYISI INEDGNEIFN TSLFEPPPPG YENVSDIVPP
    FSAFSPQGMP EGDLVYVNYA

181 RTEDFFKLER DMKINCSGKI VIARYGKVFR GNKVKNAQLA
    GAKGVILYSD PADYFAPGVK

241 SYPDGWNLPG GGVQRGNILN LNGAGDPLTP GYPANEYAYR
    RGIAEAVGLP SIPVHPIGY

301 DAQKLLEKMG GSAPPDSSWR GSLKVPYNVG PGFTGNFSTQ
    KVKMHIHSTN EVTRIYNVIG

361 TLRGAVEPDR YVILGGHRDS WVFGGIDPQS GAAVVHEIVR
    SFGTLKKEGW RPRRTILFAS

421 WDAEEFGLLG STEWAEENSR LLQERGVAYI NADSSIEGNY
    TLRVDCTPLM YSLVHNLTKE

481 LKSPDEGFEG KSLYESWTKK SPSPEFSGMP RISKLGSGND
    FEVFFQRLGI ASGRARYTKN

541 WETNKFSGYP LYHSVYETYE LVEKFYDPMF KYHLTVAQVR
    GGMVFELANS IVLPFDCRDY

601 AVVLRKYADK IYSISMKHPQ EMKTYSVSFD SLFSAVKNFT
    EIASKFSERL QDFDKSNPIV

661 LRMMNDQLMF LERAFIDPLG LPDRPFYRHV IYAPSSHNKY
    AGESFPGIYD ALFDIESKVD

721 PSKAWGEVKR QIYVAAFTVQ AAAETLSEVA
```

In one embodiment, the $V_H$ domain comprises a CDR3 selected from SEQ ID NOs. 29-33 or a sequence with at least 60%, 70%, 80% or 90% homology thereto, for example 90%, 91%, 92%, 93%, 94%, 95%, 96%, 97%, 98% or 99% homology. In one embodiment, the $V_H$ domain is selected from SEQ ID NOs. 22-26 shown in table 2b or a sequence with at least 60%, 70%, 80% or 90% homology thereto. Corresponding nucleic acid sequences are shown in table 2a. In one embodiment, said sequence homology or identity is at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%.

"Homology" generally refers to the percentage of amino acid residues in the candidate sequence that are identical with the residues of the polypeptide with which it is compared, after aligning the sequences and in some embodiments after introducing gaps, if necessary, to achieve the maximum percent homology, and not considering any conservative substitutions as part of the sequence identity. Thus, the percent homology between two amino acid sequences is equivalent to the percent identity between the two sequences. Neither N- or C-terminal extensions, tags or insertions shall be construed as reducing identity or homology. Methods and computer programs for the alignment are well known.

In one embodiment, the $V_H$ domain is selected from SEQ ID NOs. 22-26 having one or more amino acid substitutions, deletions, insertions or other modifications compared to SEQ ID NOs. 22-26, and which retains a biological function of the single domain antibody. Modifications may include one or more substitution, deletion or insertion of one or more codons encoding the single domain antibody or polypeptide that results in a change in the amino acid sequence as compared with the native sequence $V_H$ single domain antibody or polypeptide. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

In one embodiment, the modification is a conservative sequence modification. As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of a single domain antibody of the invention can be replaced with other amino acid residues from the same side chain family and the altered antibody can be tested for retained function (i.e., the functions set forth in (c) through (l) above) using the functional assays described herein.

In another embodiment, the $V_H$ domain is selected from one of the SEQ ID NOs. 22-26, but comprises one or more amino acid substitutions, for example 1 to 20, such as 1, 2, 3, 4, 5, 6, 7, 8, 9 or 10 amino acid substitutions. In one embodiment, the one or more amino acid substitution is in one or more of the framework areas. In another embodiment, the one or more amino acid substitution is in one or more of the CDRs. In one embodiment, the amino acid substitutions are in the framework and CDR sequences.

In one embodiment, the $V_H$ single domain antibody that is a variant of a single domain antibody selected from those having SEQ ID NOs. 22-26 that comprises one or more sequence modification and has improvements in one or more of a property such as binding affinity, specificity, thermostability, expression level, effector function, glycosylation, reduced immunogenicity, or solubility as compared to the unmodified single domain antibody.

A skilled person will know that there are different ways to identify, obtain and optimise the antigen binding molecules as described herein, including in vitro and in vivo expression libraries. This is further described in the examples. Optimisation techniques known in the art, such as display (e.g., ribosome and/or phage display) and/or mutagenesis (e.g., error-prone mutagenesis) can be used. The invention therefore also comprises sequence optimised variants of the single domain antibodies described herein.

The invention also relates to the use of multiple human $V_H$ domains in a CAR construct. In one embodiment, more than one, for example two or three $V_H$ domains are selected from the $V_H$ domains shown in table 2b or amino acid sequences with at least 70%, 80% or 90% homology thereto (with corresponding nucleic acids shown in table 1b).

In one embodiment, the binding domain of the CAR of the invention provides biparatopic targeting to PSMA. Thus, the binding domain comprises a first $V_H$ single domain antibody that binds to a first epitope of PSMA and a second $V_H$ single domain antibody that binds to a second epitope of PSMA. The first and second epitope may be overlapping. In one embodiment, the first $V_H$ domain comprises a CDR3 having a sequence selected from SEQ ID NOs. 29-33. In one embodiment, the first $V_H$ domain is selected from SEQ ID Nos. 22-26 shown in table 2b or from a sequence with at least 60%, 70%, 80% or 90% homology thereto.

In one embodiment, the first $V_H$ domain comprises a CDR3 having SEQ ID NOs. 31 or a sequence with at least 60%, 70%, 80% or 90% homology thereto and the second $V_H$ domain comprises a CDR3 having SEQ ID NOs. 32 or a sequence with at least 60%, 70%, 80% or 90% homology thereto. In one embodiment, the first $V_H$ domain is selected from SEQ ID No. 23 or from a sequence with at least 60%, 70%, 80% or 90% homology thereto and the second $V_H$ domain is selected from SEQ ID No. 24 or from a sequence with at least 60%, 70%, 80% or 90% homology thereto.

In one embodiment, the binding domain of the CAR of the invention provides bispecific targeting. Thus, the binding domain comprises a $V_H$ single domain antibody that binds PSMA and a second binding moiety that targets a second target. The $V_H$ single domain antibody that binds PSMA is for example selected from SEQ ID NOs. 22-26 or from a sequence with at least 60%, 70%, 80% or 90% homology thereto. The second binding moiety may be an antibody fragment, preferably a $V_H$ single domain antibody. The second target may be selected from PSCA, CS1, GPC3, CSPG4, EGFR, 5T4, L1CAM, MUC16, ROR1, cKit, ROR1, mesothelin, IL3Ra, c-Met, EGFRvII, GD-2, NY-ESO-1 TCR or MAGE A3 TCR, HER2, Wlm's tumor gene 1 (WT1), carcinoembryonic antigen (CEA), mucin 16, MUC1, an immuno checkpoint target or combinations thereof. However, a skilled person would understand that other tumor antigens are also potential combination targets within the scope of the invention.

In a preferred embodiment, a $V_H$ single domain antibody for use in a CAR as described herein is generated from human heavy chain only antibody produced in a transgenic rodent that expresses human heavy chain loci. The transgenic rodent, for example a mouse, may have a reduced capacity to express endogenous antibody genes. Thus, in one embodiment, the rodent has a reduced capacity to express endogenous light and/or heavy chain antibody genes. The rodent may therefore comprise modifications to disrupt expression of endogenous light and/or heavy chain antibody genes so that no functional light and/or heavy chains are produced.

For example, the rodent is a mouse. The mouse may comprise a non-functional endogenous lambda light chain locus. Thus, the mouse does not make a functional endogenous lambda light chain. In one embodiment, the lambda light chain locus is deleted in part or completely or rendered non-functional through insertion, inversion, a recombination event, gene editing or gene silencing. For example, at least the constant region genes C1, C2 and C3 may be deleted or rendered non-functional through insertion or other modification as described above. In one embodiment, the locus is functionally silenced so that the mouse does not make a functional lambda light chain.

Furthermore, the mouse may comprise a non-functional endogenous kappa light chain locus. Thus, the mouse does not make a functional endogenous kappa light chain. In one embodiment, the kappa light chain locus is deleted in part or completely or rendered non-functional through insertion, inversion, a recombination event, gene editing or gene silencing. In one embodiment, the locus is functionally silenced so that the mouse does not make a functional kappa light chain.

The mouse having functionally-silenced endogenous lambda and kappa L-chain loci may, for example, be made as disclosed in WO 2003/000737, which is hereby incorporated by reference in its entirety.

Furthermore, the mouse may comprise a non-functional endogenous heavy chain locus. Thus, the mouse does not make a functional endogenous heavy chain. In one embodiment, the heavy chain locus is deleted in part or completely or rendered non-functional through insertion, inversion, a recombination event, gene editing or gene silencing. In one embodiment, the locus is functionally silenced so that the mouse does not make a functional heavy chain.

For example, as described in WO 2004/076618 (hereby incorporated by reference in its entirety), all 8 endogenous heavy chain constant region immunoglobulin genes (μ, δ, γ3, γ1, γ2a, γ2b, ε and α) are absent in the mouse, or partially absent to the extent that they are non-functional, or genes δ, γ3, γ1, γ2a, γ2b and F are absent and the flanking genes μ and α are partially absent to the extent that they are rendered non-functional, or genes μ, δ, γ3, γ1, γ2a, γ2b and ε are absent and α is partially absent to the extent that it is rendered non-functional, or δ, γ3, γ1, γ2a, γ2b, ε and α are absent and μ is partially absent to the extent that it is rendered non-functional. By deletion in part is meant that the endogenous locus gene sequence has been deleted or disrupted, for example by an insertion, to the extent that no functional endogenous gene product is encoded by the locus, i.e., that no functional product is expressed from the locus. In another embodiment, the locus is functionally silenced.

For example, the mouse comprises a non-functional endogenous heavy chain locus, a non-functional endogenous lambda light chain locus and a non-functional endogenous kappa light chain locus. The mouse therefore does not produce any functional endogenous light or heavy chains. Thus, the mouse is a triple knockout (TKO) mouse.

The transgenic mouse may comprise a vector, for example a Yeast Artificial Chromosome (YAC) for expressing a heterologous heavy chain locus. YACs are vectors that can be employed for the cloning of very large DNA inserts in yeast. As well as comprising all three cis-acting structural elements essential for behaving like natural yeast chromosomes (an autonomously replicating sequence (ARS), a centromere (CEN) and two telomeres (TEL)), their capacity to accept large DNA inserts enables them to reach the minimum size (150 kb) required for chromosome-like stability and for fidelity of transmission in yeast cells. The construction and use of YACs is well known in the art (e.g., Bruschi, C. V. and Gjuracic, K. Yeast Artificial Chromosomes, Encyclopedia of Life Sciences, 2002 Macmillan Publishers Ltd, Nature Publishing Group/www.els.net).

For example, the YAC may comprise a plethora of human $V_H$, D and J genes in combination with mouse immunoglobulin constant region genes lacking $C_H1$ domains, mouse enhancer and regulatory regions.

Alternative methods known in the art may be used for deletion or inactivation of endogenous mouse or rat immunoglobulin genes and introduction of human $V_H$, D and J genes in combination with mouse immunoglobulin constant region genes lacking $C_H1$ domains, mouse enhancer and regulatory regions.

Transgenic mice can be created according to standard techniques as illustrated in the examples. The two most characterised routes for creating transgenic mice are via pronuclear microinjection of genetic material into freshly fertilised oocytes or via the introduction of stably transfected embryonic stem cells into morula or blastocyst stage embryos. Regardless of how the genetic material is introduced, the manipulated embryos are transferred to pseudopregnant female recipients where pregnancy continues and candidate transgenic pups are born.

The main differences between these broad methods are that ES clones can be screened extensively before their use to create a transgenic animal. In contrast, pronuclear microinjection relies on the genetic material integrating to the host genome after its introduction and, generally speaking, the successful incorporation of the transgene cannot be confirmed until after pups are born.

There are many methods known in the art to both assist with and determine whether successful integration of transgenes occurs. Transgenic animals can be generated by multiple means including random integration of the construct into the genome, site-specific integration, or homologous recombination. There are various tools and techniques that can be used to both drive and select for transgene integration and subsequent modification including the use of drug resistance markers (positive selection), recombinases, recombination-mediated cassette exchange, negative selection techniques, and nucleases to improve the efficiency of recombination. Most of these methods are commonly used in the modification of ES cells. However, some of the techniques may have utility for enhancing transgenesis mediated via pronuclear injection.

Further refinements can be used to give more efficient generation of the transgenic line within the desired background. As described above, in preferred embodiments, the endogenous mouse immunoglobulin expression is silenced to permit sole use of the introduced transgene for the expression of the heavy-chain only repertoire that can be exploited for drug discovery. Genetically-manipulated mice, for example TKO mice that are silenced for all endogenous immunoglobulin loci (mouse heavy chain, mouse kappa chain and mouse lambda chain) can be used as described above. The transfer of any introduced transgene to this TKO background can be achieved via breeding, (either conventional or with the inclusion of an IVF step to give efficient scaling of the process). However, it is also possible to include the TKO background during the transgenesis procedure. For example, for microinjection, the oocytes may be derived from TKO donors. Similarly, ES cells from TKO embryos can be derived for use in transgenesis. Triple knock-out mice into which transgenes have been introduced are referred to herein as TKO/Tg. In one embodiment, the mouse is as described in WO 2016/062990.

The transgenic rodent described above produces human variable heavy chains which can be isolated and used for the generation of human $V_H$ domains for use in the CARs of the invention, for example as described in WO 2016/062990 or WO 2016/113557.

Thus, the invention also relates to a CAR comprising a single $V_H$ domain antibody generated from human variable heavy chains produced in a TKO mouse that expresses human heavy chain loci.

In addition to a binding domain as described in detail above, the CAR of the invention further comprises a transmembrane domain. A "transmembrane domain" (TMD) as used herein refers to the region of the CAR which crosses the plasma membrane and is connected to the endoplasmic signaling domain and the antigen binding domain, in case of the latter optionally via a hinge. In one embodiment, the transmembrane domain of the CAR of the invention is the transmembrane region of a transmembrane protein (for example Type I transmembrane proteins), an artificial hydrophobic sequence or a combination thereof. In one embodiment, the transmembrane domain comprises the CD3zeta domain or CD28 transmembrane domain. Other transmembrane domains will be apparent to those of skill in the art and may be used in connection with alternate embodiments of the invention.

Specifically within the scope of invention are TM sequences shown in table 1.

The CAR of the invention further comprises an intracellular signaling domain. An "intracellular signaling domain", "cytoplasmic domain" or "endodomain" is the domain that transmits activation signals to T cells and directs the cell to perform its specialized function. Examples of domains that transduce the effector function signal and can be used accoridng to the invention include but are not limited to the ζ chain of the T-cell receptor complex or any of its homologs (e.g., η chain, FcsRly and β chains, MB 1 (Iga) chain, B29 (Ig) chain, etc.), human CD3zeta chain, CD3 polypeptides (Δ, δ and ε), syk family tyrosine kinases (Syk, ZAP 70, etc.), src family tyrosine kinases (Lck, Fyn, Lyn, etc.) and other molecules involved in T-cell transduction, such as CD2. CD5, OX40 and CD28. Other intracellular signaling domains will be apparent to those of skill in the art and may be used in connection with alternate embodiments of the invention. In one embodiment, the TM domain is obtained from CD28.

Specifically within the scope of invention are intracellular signaling domain sequences shown in table 1.

In one embodiment, the CAR of the invention further comprises one or more co-stimulatory domains to enhance CAR-T cell activity after antigen specific engagement. Inclusion of this domain in the CAR of the invention enhances the proliferation, survival and/or development of memory cells. The co-stimulatory domain is located intracellularly. The co-stimulatory domain is a functional signaling domain obtained from a protein selected form the following group: CD28, CD137 (4-IBB), CD134 (OX40), DapIO, CD27, CD2, CD5, ICAM-1, LFA-1(CD1 Ia/CD18), Lck, TNFR-I. TNFR-II, Fas, CD30, CD40 or combinations thereof. Other co-stimulatory domains (e.g., from other proteins) will be apparent to those of skill in the art. Multiple co-stimulatory domains can be included in a single CAR to recruit multiple signaling pathways. In one embodiment, the co-stimulatory domain is obtained from 4-1BB. The term "4-1BB" refers to a member of the TNFR superfamily with an amino acid sequence provided as GenBank Acc. No. AAA62478.2, or the equivalent residues from a non-human species, e.g., rodent (e.g. mouse or rat), monkey or ape. The term "4-1BB costimulatory domain" refers to amino acid residues 214-255 of GenBank Acc. No. AAA62478.2, or the equivalent residues from a non-human species, e.g., mouse, rodent, monkey, ape and the like.

Specifically within the scope of invention are co-stimulatory domains sequences shown in table 1.

In one embodiment, the CAR of the invention further comprises a hinge or spacer region which connects the extracellular antigen binding domain and the transmembrane domain. This hinge or spacer region can be used to achieve different lengths and flexibility of the resulting CAR. Examples of the a hinge or spacer region that can be used according to the invention include, but are not limited to, Fc fragments of antibodies or fragments or derivatives thereof, hinge regions of antibodies, or fragments or derivatives thereof, $C_H2$ regions of antibodies, $C_H3$ regions of antibodies, artificial spacer sequences, for example peptide sequences, or combinations thereof. Other hinge or spacer region will be apparent to those of skill in the art and may be used in connection with alternate embodiments of the invention. In one embodiment, the hinge is an IgG4 hinge or a CD8A hinge.

Specifically within the scope of invention are hinge sequences shown in table 1.

In one embodiment, the CAR of the invention further comprises a "linker domain" or "linker region" that connects different domains of the CAR. This domain includes an oligo- or polypeptide region from about 1 to 100 amino acids in length. Suitable linkers will be apparent to those of skill in the art and may be used in connection with alternate embodiments of the invention.

In one embodiment, the CAR of the invention further comprises a "leader sequence". In one embodiment, the leader sequence is a CD8A domain. Specifically within the scope of invention are leader sequences shown in table 1.

In one embodiment, the CAR comprises at least two antigen-specific binding domains (each comprising a single $V_H$ domain antibody), an extracellular leader domain, an extracellular spacer domain, a transmembrane domain, one or more co-stimulatory domains and an intracellular signaling domain. In one embodiment, the CAR comprises the components as shown in table 1a (having the amino acids as shown in table 2a or amino acid sequences with at least 70%, 80% or 90% homology thereto, with corresponding nucleic acid sequences shown in table 1a) together with an antigen binding domain comprising two or three $V_H$ domains selected from the $V_H$ domains shown in table 2b or amino acid sequences with at least 70%, 80% or 90% homology thereto (with corresponding nucleic acids shown in table 1b).

In some aspects, the CAR of the invention includes an antigen binding domain that transmits an inhibitory signal.

The CAR may further include a label, for example a label that facilitates imaging, such as a fluorescent label or other tag. This can, for example be used in methods for imaging tumor binding. The label may be conjugated to the antigen binding domain.

The CARs described herein may be synthesized as single polypeptide chains. In this embodiment, the antigen-specific targeting regions are at the N-terminus, arranged in tandem and are separated by a linker peptide.

In another aspect, the invention relates to an isolated nucleic acid construct comprising at least one nucleic acid encoding a CAR as defined above. In one embodiment, the nucleic acid encodes a protein that targets one of the targets listed herein. In a preferred embodiment, the target is PSMA. Suitable CAR sequences within the scope of the invention are shown in tables 1 and 2. Also within the scope of the invention are sequences with at least 60%, 70%, 80% or 90% homology thereto. The term "nucleic acid," "polynucleotide," or "nucleic acid molecule" refers to deoxyribonucleic acid (DNA) or ribonucleic acid (RNA), or a combination of a DNA or RNA. RNA includes in vitro transcribed RNA or synthetic RNA; an mRNA sequence encoding a CAR polypeptide as described herein). The nucleic acid may further comprise a suicide gene. The construct may be in the form of a plasmid, vector, transcription or expression cassette.

In one embodiment, the vector is an in vitro transcribed vector, e.g., a vector that transcribes RNA of a nucleic acid molecule described herein. The expression vector may be provided to a cell in the form of a viral vector. Viral vector technology is well known in the art and is described, for example, in Sambrook et al. (Molecular Cloning: A Laboratory Manual, Cold Spring Harbor Laboratory, New York, 2013). A number of viral based systems have been developed for gene transfer into mammalian cells. For example, retroviruses such as, adenovirus vectors are used. In one embodiment, a lentivirus vector is used. This is demonstrated in the examples. The invention also relates to a virus comprising a CAR described above.

In a further aspect, the invention also relates to an isolated cell or cell population comprising one or more nucleic acid construct as described above. The cell has thus been genetically modified to express a CAR nucleic acid construct of the invention. Thus, the invention provides genetically engineered cells which comprise and stably express a CAR nucleic acid construct of the invention. In one embodiment, the cell is selected from the group consisting of a T cell, a Natural Killer (NK) cell, a cytotoxic T lymphocyte (CTL), a regulatory T cell, hematopoietic stem cells and/or pluripotent embryonic/induced stem cells. T cells may be isolated from a patient for transfection with a CAR nucleic acid construct of the invention.

For example, cells can be transfected with the nucleic acid of the invention ex vivo. Various methods produce stable transfectants which express a CARs of the invention. In one embodiment, a method of stably transfecting and re-directing cells is by electroporation using naked DNA. Additional methods to genetically engineer cells using naked DNA encoding a CAR of the invention include but are not limited to chemical transformation methods (e.g., using calcium phosphate, dendrimers, liposomes and/or cationic polymers), non-chemical transformation methods (e.g., electroporation, optical transformation, gene electrotransfer and/or hydrodynamic delivery) and/or particle-based methods (e.g., impalefection, using a gene gun and/or magnetofection). The transfected cells demonstrating presence of an integrated un-rearranged vector and expression of the CAR may be expanded ex vivo. Viral transduction methods may also be used to generate redirected cells which express the CAR of the invention.

Cells that express a CAR of the invention are used in the treatment of disease.

The invention thus relates to methods for the prevention and/or treatment of cancer, comprising administering to a subject a cell or cell population comprising a CAR as described herein, said method comprising administering, to a subject in need thereof, a pharmaceutically active amount of a cell and/or of a pharmaceutical composition of the invention.

The invention also relates to a CAR, a cell or cell population comprising a CAR as described herein for use in therapy. The invention also relates to a CAR or a cell comprising a CAR as described herein for use in the treatment of cancer. The invention also relates to the use of a CAR or a cell comprising a CAR as described herein in the manufacture of a medicament for the treatment of cancer.

In another aspect, the invention relates to a method for stimulating a T cell-mediated immune response to a target cell population or tissue in a subject, the method comprising administering to a subject an effective amount of a cell or cell population that expresses a CAR of the invention, wherein the antigen binding domain is selected to specifically recognize the target cell population or tissue.

In another aspect, the invention relates to a method of providing an anti-tumor immunity in a subject, the method comprising administering to the mammal an effective amount of a cell or cell population genetically modified to express a CAR of the invention, thereby providing an anti-tumor immunity in the subject.

In another aspect, the invention relates to a method for producing a genetically modified cell or cell population comprising expressing in said cell or cell population a CAR nucleic acid construct of the invention. The method may include introducing into the cell a nucleic acid as described herein (e.g., an in vitro transcribed RNA or synthetic RNA: an mRNA sequence encoding a CAR polypeptide as described herein). In embodiments, the RNA expresses the CAR polypeptide transiently. In one embodiment, the cell is a cell as described herein, e.g., an immune effector cell (e.g., T cells or NK cells, or cell population). Cells produced by such methods are also within the scope of the invention.

In another aspect, the invention relates to an ex vivo method for generating a population of cells for use in adaptive immunotherapy comprising transforming said cell with a CAR of the invention.

In another aspect of the present invention, there is provided a pharmaceutical composition comprising a CAR or an isolated cell or cell population comprising a CAR according to the present invention and optionally a pharmaceutically acceptable carrier.

The genetically modified cells or pharmaceutical composition of the present invention can be administered by any convenient route, including parenteral administration. Parenteral administration includes, for example, intravenous, intramuscular, intraarterial, intraperitoneal, intranasal, rectal, intravesical, intradermal, topical or subcutaneous administration. Compositions can take the form of one or more dosage units.

The composition of the invention can be in the form of a liquid, e.g., a solution, emulsion or suspension. The liquid can be useful for delivery by injection, infusion (e.g., IV infusion) or sub-cutaneously. The liquid compositions of the invention, whether they are solutions, suspensions or other like form, can also include one or more of the following: sterile diluents such as water, saline solution, preferably physiological saline, Ringer's solution, isotonic sodium chloride, fixed oils such as synthetic mono or diglycerides, polyethylene glycols, glycerin, or other solvents; antibacterial agents such as benzyl alcohol or methyl paraben; and agents for the adjustment of tonicity such as sodium chloride or dextrose. A composition can be enclosed in an ampoule, a disposable syringe or a multiple-dose vial made of glass, plastic or other material.

The amount of the pharmaceutical composition of the present invention that is effective/active in the treatment of a particular disorder or condition will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances.

The compositions of the invention comprise an effective amount of a binding molecule of the present invention such that a suitable dosage will be obtained. The correct dosage of the compounds will vary according to the particular formulation, the mode of application, and its particular site, host and the disease being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

Typically, this amount is at least about 0.01% of a binding molecule of the present invention by weight of the composition.

Preferred compositions of the present invention are prepared so that a parenteral dosage unit contains from about 0.01% to about 2% by weight of the binding molecule of the present invention.

For intravenous administration, the composition can comprise from about typically about 0.1 mg/kg to about 250 mg/kg of the animal's body weight, preferably, between about 0.1 mg/kg and about 20 mg/kg of the animal's body weight, and more preferably about 1 mg/kg to about 10 mg/kg of the animal's body weight.

The present compositions can take the form of suitable carriers, such aerosols, sprays, suspensions, or any other form suitable for use. Other examples of suitable pharmaceutical carriers are described in "Remington's Pharmaceutical Sciences" by E. W. Martin.

The pharmaceutical compositions can be prepared using methodology well known in the pharmaceutical art. For example, a composition intended to be administered by injection can be prepared by combining a binding molecule of the present invention with water so as to form a solution. A surfactant can be added to facilitate the formation of a homogeneous solution or suspension.

The pharmaceutical composition of the invention can be co-administered with other therapeutics, for example anti-cancer agents.

In one embodiment, the cancer is selected from a haematological cancer or malignancy or a solid tumor. Hematologic cancers are cancers of the blood or bone marrow. Solid tumors are abnormal masses of tissue that usually do not contain cysts or liquid areas.

In one embodiment, the cancer is metastatic.

Cancers that may treated by methods, uses and compositions described herein include, but are not limited to, cancer cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

In one embodiment, the CAR is used to target PSMA and treat prostate cancer. Such a CAR includes an antigen binding domain specific to PSMA as described herein.

In therapies of prostatic disorders, e.g., prostate cancer, the therapy can be used in combination with existing therapies. In one embodiment, a CAR or cell comprising a CAR of the invention is used in combination with an existing therapy or therapeutic agent, for example an anti-cancer therapy. Thus, in another aspect, the invention also relates to a combination therapy comprising administration of a CAR-T or pharmaceutical composition of the invention and an anti-cancer therapy. The anti-cancer therapy may include a therapeutic agent or radiation therapy and includes gene therapy, viral therapy, RNA therapy bone marrow transplantation, nanotherapy, targeted anti-cancer therapies or oncolytic drugs. Examples of other therapeutic agents include other checkpoint inhibitors, antineoplastic agents, immunogenic agents, attenuated cancerous cells, tumor antigens, antigen presenting cells such as dendritic cells pulsed with tumor-derived antigen or nucleic acids, immune stimulating cytokines (e.g., IL-2, IFNa2, GM-CSF), targeted small molecules and biological molecules (such as components of signal transduction pathways, e.g. modulators of tyrosine kinases and inhibitors of receptor tyrosine kinases, and agents that bind to tumor-specific antigens, including EGFR antagonists), an anti-inflammatory agent, a cytotoxic agent, a radiotoxic agent, or an immunosuppressive agent and cells transfected with a gene encoding an immune stimulating cytokine (e.g., GM-CSF), chemotherapy. In one embodiment, the CAR-T or pharmaceutical composition of the invention is used in combination with surgery. The CAR-T or pharmaceutical composition of the invention may be administered at the same time or at a different time as the other therapy, e.g., simultaneously, separately or sequentially.

In another aspect, the invention provides a kit for detecting cancer, for example prostate cancer for diagnosis, treatment, prognosis or monitoring comprising a genetically modified cell or pharmaceutical composition of the invention. The kit may also comprise instructions for use. In one embodiment, the CAR-T or pharmaceutical composition comprises a label and one or more compounds for detecting the label. The invention in another aspect provides a binding molecule of the invention packaged in lyophilized form, or packaged in an aqueous medium.

The invention also relates to a CAR as set forth in accompanying FIG. 3 or 4.

Unless otherwise defined herein, scientific and technical terms used in connection with the present disclosure shall have the meanings that are commonly understood by those of ordinary skill in the art. While the foregoing disclosure provides a general description of the subject matter encompassed within the scope of the present invention, including methods, as well as the best mode thereof, of making and using this invention, the following examples are provided to further enable those skilled in the art to practice this invention and to provide a complete written description thereof. However, those skilled in the art will appreciate that the specifics of these examples should not be read as limiting on the invention, the scope of which should be apprehended from the claims and equivalents thereof appended to this disclosure. Various further aspects and embodiments of the present invention will be apparent to those skilled in the art in view of the present disclosure.

All documents and sequence database identifiers mentioned in this specification are incorporated herein by reference in their entirety.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein. Unless context dictates otherwise, the descriptions and definitions of the features set out above are not limited to any particular aspect or embodiment of the invention and apply equally to all aspects and embodiments which are described.

The invention is further described in the non-limiting examples.

EXAMPLES

Example 1. Design and Cloning of CART Constructs

Construction of Tg/TKO Mice

Mice carrying a heavy-chain antibody transgenic locus in germline configuration within a background that is silenced for endogenous heavy and light chain antibody expression (triple knock-out, or TKO) were created as previously described (WO2004/076618 and WO2003/000737, Ren et al., Genomics, 84, 686, 2004; Zou et al., J. Immunol., 170, 1354, 2003). Briefly, transgenic mice were derived following pronuclear microinjection of freshly fertilised oocytes with a yeast artificial chromosome (YAC) comprising a plethora of human $V_H$, D and J genes in combination with mouse immuoglobulin constant region genes lacking 20 CH1 domains, mouse enhancer and regulatory regions. Yeast artificial chromosomes (YACs) are vectors that can be employed for the cloning of very large DNA inserts in yeast. As well as comprising all three cis-acting structural elements essential for behaving like natural yeast chromosomes (an autonomously replicating sequence (ARS), a centromere (CEN) and two telomeres (TEL)), their capacity to accept large DNA inserts enables them to reach the minimum size (150 kb) required for chromosome-like stability and for fidelity of transmission in yeast cells. The construction and use of YACs is well known in the art (e.g., Bruschi, C. V. and Gjuracic, K. Yeast Artificial Chromosomes. Encyclopedia of Life Sciences, 2002, Macmillan Publishers Ltd., Nature Publishing Group/e!s.net).

The YAC used comprised multiple human heavy chain V genes, human heavy chain D and J genes. It lacks the $C_H1$ exon.

The transgenic founder mice were back crossed with animals that lacked endogenous immunoglobulin expression to create the Tg/TKO lines used for immunisation with recombinant PSMA antigen. Libraries were generated from immunised mice and PSMA binders were selected employing assays for target binding, including ELISA. Octet analysis was used to measure binding kinetics. PSMA binders listed in table 2 show specificity for the PSMA antigen.

The CAR-T constructs used in the following experiments include a $V_H$ that recognises a PSMA antigen. The elements of the constructs are set out further below.

Extracellular Domain

Signal Peptide

A signal peptide directs the nascent protein into the endoplasmic reticulum. This is used if the receptor is to be glycosylated and anchored in the cell membrane.

Antigen Recognition Region

The antigen recognition domain is a $V_H$ domain. This may be specific for a tumour target (e.g. PSMA) or an irrelevant $V_H$ (HEL). An antigen recognition domain may optionally have a His tag for recognition.

Spacer

A spacer region links the antigen binding domain to the transmembrane domain. It should be flexible enough to allow the antigen binding domain to orient in different directions to facilitate antigen recognition.

Transmembrane Domain

The transmembrane domain is a hydrophobic alpha helix that spans the membrane. Generally, the transmembrane domain from the most membrane proximal component of the endodomain is used.

Intracellular Domain

After antigen recognition, receptors cluster and a signal is transmitted to the cell. The most commonly used endodomain component is CD3-zeta which contains 3 ITAMs. This transmits an activation signal to the T cell after antigen is bound. CD3-zeta may not provide a fully competent activation signal and additional co-stimulatory signaling is needed. For example, chimeric CD28 and OX40 or CD137 can be used with CD3zeta to transmit a proliferative/survival signal, or all three can be used together.

Each construct has either a long hinge or a short hinge. Constructs are assembled as follow:

Leader-$V_H$-hinge-CD28 TM and signal-4-1BB signal-CD3zeta signal

TABLE 1a

Nucleic acid sequence of component parts

| Gene | Ensembl ID | Amino acids | Sequence |
|---|---|---|---|
| Leader | CD8A | CD8A-001 | 1-21 | ATGGCCTTACCAGTGACCGC CTTGCTCCTGCCGCTGGCCT TGCTGCTCCACGCCGCCAGG CCG SEQ ID NO: 1 |
| $V_H$ | | | | See below |
| Long hinge | CD8A | CD8A-001 | 138-182 | ACCACGACGCCAGCGCCGCG ACCACCAACACCGGCGCCCA CCATCGCGTCGCAGCCCCTG TCCCTGCGCCCAGAGGCGTG CCGGCCAGCGGCGGGGGGCG CAGTGCACACGAGGGGGCTG GACTTCGCCTGTGAT SEQ ID NO: 2 |
| Short hinge | IgG4 | IGHG4-001 | 99-111 | GAGTCCAAATATGGTCCCCC ATGCCCATCATGCCCAGCA SEQ ID NO: 3 |
| TM & signal 1 | CD28 | CD28-001 | 153-220 | TTTTGGGTGCTGGTGGTGGT TGGTGGAGTCCTGGCTTGCT ATAGCTTGCTAGTAACAGTG GCCTTTATTATTTTCTGGGT GAGGAGTAAGAGGAGCAGGC TCCTGCACAGTGACTACATG |

Note: Column headers align as Gene | Ensembl ID | Amino acids | Sequence (4 columns for data). The table above has been shown with an extra leading column for clarity.

TABLE 1a-continued

Nucleic acid sequence of component parts

| Gene | | Ensembl ID | Amino acids | Sequence |
|---|---|---|---|---|
| | | | | AACATGACTCCCCGCCGCC CGGGCCCACCCGCAAGCATT ACCAGCCCTATGCCCCACCA CGCGACTTCGCAGCCTATCG CTCC<br>SEQ ID NO: 4 |
| Signal 2 | 4-1BB | TNFRSF9-001 | 214-255 | AAACGGGGCAGAAAGAAACT CCTGTATATATTCAAACAAC CATTTATGAGACCAGTACAA ACTACTCAAGAGGAAGATGG CTGTAGCTGCCGATTTCCAG AAGAAGAAGAAGGAGGATGT GAACTG<br>SEQ ID NO: 5 |
| Signal 3 | CD3 zeta | CD247-002 | 52-164 | AGAGTGAAGTTCAGCAGGAG CGCAGACGCCCCCGCGTACC AGCAGGGCCAGAACCAGCTC TATAACGAGCTCAATCTAGG ACGAAGAGAGGAGTACGATG TTTTGGACAAGAGACGTGGC CGGGACCCTGAGATGGGGGG AAAGCCGCAGAGAAGGAAGA ACCCTCAGGAAGGCCTGTAC AATGAACTGCAGAAAGATAA GATGGCGGAGGCCTACAGTG AGATTGGGATGAAAGGCGAG CGCCGGAGGGGCAAGGGGCA CGATGGCCTTTACCAGGGTC TCAGTACAGCCACCAAGGAC ACCTACGACGCCCTTCACAT GCAGGCCCTGCCCCCTCGCT AA<br>SEQ ID NO: 6 |

TABLE 1b

Protein sequence of component parts

| Gene | | Ensembl ID | Amino acids | Sequence |
|---|---|---|---|---|
| Leader | CD8A | CD8A-001 | 1-21 | MALPVTALLLPLALLLHAAR P<br>SEQ ID NO: 7 |
| Long hinge | CD8A | CD8A-001 | 138-182 | TTTPAPRPPTPAPTIASQPL SLRPEACRPAAGGAVHTRGL DFACD<br>SEQ ID NO: 8 |
| Short hinge | IgG4 | IGHG4-001 | 99-111 | ESKYGPPCPSCPA<br>SEQ ID NO: 9 |
| TM & signal 1 | CD28 | CD28-001 | 153-220 | FWVLVVVGGVLACYSLLVTV AFIIFWVRSKRSRLLHSDYM NMTPRRPGPTRKHYQPYAPP RDFAAYRS<br>SEQ ID NO: 10 |
| Signal 2 | 4-1BB | TNFRSF9-001 | 214-255 | KRGRKKLLYIFKQPFMRPVQ TTQEEDGCSCRFPEEEEGGC EL<br>SEQ ID NO: 11 |
| Signal 3 | CD3 zeta | CD247-002 | 52-164 | RVKFSRSADAPAYQQGQNQL YNELNLGRREEYDVLDKRRG RDPEMGGKPQRRKNPQEGLY NELQKDKMAEAYSEIGMKGE |

TABLE 1b-continued

Protein sequence of component parts

| Gene | Ensembl ID | Amino acids | Sequence |
|---|---|---|---|
| | | | RRRGKGHDGLYQGLSTATKD TYDALHMQALPPR<br>SEQ ID NO: 12 |

All co-ordinates correspond to Ensembl database entries ensembl.org

TABLE 2a

Anti-PSMA V$_H$ nucleic acid sequences used in CAR-T constructs; HB = Humabody ®

| V$_H$ | sequence |
|---|---|
| HEL (control) | GTCCAATTGCTGGAGAGCGGTGGTGGTCTGGTGCAGCCGG GTGGCTCCCTGCGTCTGAGCTGTGCGGCGAGCGGCTTCCG CATCAGCGACGAGGACATGGGTTGGGTGCGTCAGGCACCG GGCAAGGGCCTGGAGTGGGTTTCTAGCATTTACGGTCCGA GCGGTAGCACCTATTACGCAGACAGCGTGAAAGGTCGTTT TACGATCAGCCGCGATAATTCCAAGAACACGTTGTATCTG CAAATGAACAGCCTGCGTGCGGAAGATACCGCAGTTTACT ATTGCGCGTCTGCGCTGGAACCGCTGAGCGAGCCACTGGG CTTCTGGGGTCAAGGCACCCTGGTTACTGTCTCGAGC<br>SEQ ID NO: 13 |
| HEL-His tag (control) | GTCCAATTGCTGGAGAGCGGTGGTGGTCTGGTGCAGCCGG GTGGCTCCCTGCGTCTGAGCTGTGCGGCGAGCGGCTTCCG CATCAGCGACGAGGACATGGGTTGGGTGCGTCAGGCACCG GGCAAGGGCCTGGAGTGGGTTTCTAGCATTTACGGTCCGA GCGGTAGCACCTATTACGCAGACAGCGTGAAAGGTCGTTT TACGATCAGCCGCGATAATTCCAAGAACACGTTGTATCTG CAAATGAACAGCCTGCGTGCGGAAGATACCGCAGTTTACT ATTGCGCGTCTGCGCTGGAACCGCTGAGCGAGCCACTGGG CTTCTGGGGTCAAGGCACCCTGGTTACTGTCTCGAGCGCG GCCGCACACCACCACCATCACCAT<br>SEQ ID NO: 14 |
| HB1 | GAGGTGCAGCTGGTGGAGTCTGGGGGAGGCGTGGTCCAGC CTGGGAGGTCCCTGAGACTCTCCTGTGCAGCCTCTGGATT CCCCTTAATTAGCTATGGCATGCACTGGGTCCGCCAGGCT CCAGGCAAGGGGCTGGAGTGGGTGGCATTTATGACATATG ATGGAAGTAATAGATACTATGCAGACTCCGTGAAGGGCCG ATTCACCATCTCCAGAGACAATTCCAAGAACACGCTGTAT CTGCAAATGAACAGCCTGAGAGATGAGGACACGGCTCTAT ATTACTGTGCGAGAGATCGTATAGTGGGAGGTAGGGTCCC TGATGCTTTTGATATCTGGGGCCAAGGGACAATGGTCACC GTCTCTTCA<br>SEQ ID NO:15 |
| HB2 | GAGGTGCAGCTGTTGGAGTCTGGGGGAGGCTTGGTACAGC CTGGGGGGTCCCTGAGACTCTCCTGTGCAGCCTCTGGATT CAGTTTTAGCAGCTATGCCATGAGTTGGGTCCGCCAGGCT CCAGGGAAGGGGCTGGAGTGGGTCTCAAGTATTGGTGAGA ATGATGGTACCACAGACTACGCAGACTCCGTGAAGGGCCG ATTCACCATCTCCAGAGACAATTCCAAGAGTATGCTGTAT CTGCAAATGAACAGCCTGAGAGTCGAGGACACGGCCGTCT ATTACTGTGTGAAAGATGGTGTCCACTGGGGCCAGGGAAC CCTGGTCACCGTCTCCTCA<br>SEQ ID NO: 16 |
| HB3 | GAGGTGCAGCTGGTGGAGTCTGGGGGAGGCGTGGTCCAGC CTGGGAGGTCCCTGAGACTCTCCTGTGCAGCCTCTGGATT CCCTTCAGTGGCTATGGCATGCACTGGGTCCGCCAGGCT CCAGGCAAGGGACTGGAGTGGGTGGCATATATATCATATG ATGGAAGTAATAAATACTATGCAGACTCCGTGAAGGGCCG ATTCACCATCTCCAGAGACAATTCCAAGAACACGCTGTAT CTGCAAATGAACAGCCTGAGAGCTGAGGACACGGCTGTGT ATTACTGTGCGAAAGATCCGGCCTGGGGATTACGTTTGGG GGAGTCATCGTCCTATGATTTTGATATCTGGGGCCAAGGG ACAATGGTCACTGTCTCTTCA<br>SEQ ID NO: 17 |

TABLE 2a-continued

Anti-PSMA $V_H$ nucleic acid sequences used in CAR-T constructs; HB = Humabody ®

| $V_H$ | sequence |
|---|---|
| HB4 | CAGGTGCAGCTGCAGGAGTCGGGCGCAGGACTGTTGAAGC<br>CTTCGGAGACCCTGTCCCTCACCTGCGCTGTCTATGGTGG<br>GTCCTTCAGTGCTTACAACTGGAACTGGATCCGCCAGCCC<br>CCCGGGAAGGGGCTGGAGTGGATTGGGGAAATCAATCATA<br>GGGGAGACACCGCCTACAACCCGTCCCTCAAGAGTCGAGT<br>CACCATATCAGTAGACACGTCCAAGAATCAGTTCTCCCTG<br>AACCTGACCTCTGTGACCGCCGCGGACACGGCTGTGTATT<br>ACTGTGCGGCACGTGGATATAGCTATGGTTGGCCCCCCGG<br>ATATATCAGTGACTCCTTTGACTACTGGGGCCAGGGAACC<br>CAGGTCACTGTCTCTTCA<br>SEQ ID NO. 18 |
| HB5 | CAGGTGCAGCTACAGGAGTCGGGCCCAGGACTGGTGAAGC<br>CTTCACAGACCCTGTCCCTCACCTGCACTGTCTCTGGTGG<br>CTCCATCAGCAATAGTGGTTATTACTGGAGCTGGGTCCGC<br>CAGCACCCAGGGAAGGACCTGGAGTGGATTGGGTTCATCT<br>ATTACAATGGGAGCATCCACTACAACCCGTCCCTCAAGAG<br>TCGAGTTATCATATCAGTAGACACGTCTAAGAACCAGTTC<br>TCCCTGAAAATGAACTCTGTGACTGCCGCGGACACGGCCG<br>TGTATTACTGTGCGAGAGACGGGGATGACTACGGTGACTA<br>CTTGAGGGGCCAGGGAACCCTGGTCACCGTCTCCTCA<br>SEQ ID NO. 19 |

TABLE 2b

Anti-PSMA $V_H$ amino acid sequences used in CAR constructs.

| $V_H$ | sequence |
|---|---|
| HEL | VQLLESGGGLVQPGGSLRLSCAASGFRISDEDMGWVRQA<br>PGKGLEWVSSIYGPSGSTYYADSVKGRFTISRDNSKNTL<br>YLQMNSLRAEDTAVYYCASALEPLSEPLGFWGQGTLVTV<br>SEQ ID NO: 20 |
| HEL-His tag | VQLLESGGGLVQPGGSLRLSCAASGFRISDEDMGWVRQA<br>PGKGLEWVSSIYGPSGSTYYADSVKGRFTISRDNSKNTL<br>YLQMNSLRAEDTAVYYCASALEPLSEPLGFWGQGTLVTV<br>SSAAAHHHHHH<br>SEQ ID NO: 21 |
| HB1 | EVQLVESGGGVVQPGRSLRLSCAASGFPLISYGMHWVRQ<br>APGKGLEWVAFMTYDGSNRYYADSVKGRFTISRDNSKNT<br>LYLQMNSLRDEDTALYYCARDRIVGGRVPDAFDIWGQGT<br>MVTVSS<br>SEQ ID NO: 22<br>CDR3: DRIVGGRVPDAFDI (SEQ ID NO: 29) |
| HB2 | EVQLLESGGGLVQPGGSLRLSCAASGFSFSSYAMSWVRQ<br>APGKGLEWVSSIGENDGTTDYADSVKGRFTISRDNSKSM<br>LYLQMNSLRVEDTAVYYCVKDGVHWGQGTLVTVSS<br>SEQ ID NO: 23<br>CDR3: DGVH (SEQ ID NO: 30) |
| HB3 | EVQLVESGGGVVQPGRSLRLSCAASGFSFSGYGMHWVRQ<br>APGKGLEWVAYISYDGSNKYYADSVKGRFTISRDNSKNT<br>LYLQMNSLRAEDTAVYYCAKDPAWGLRLGESSSYDFDIW<br>GQGTMVTVSS<br>SEQ ID NO: 24<br>CDR3: DPAWGLRLGESSSYDFDI (SEQ ID NO: 31) |
| HB4 | QVQLQESGAGLLKPSETLSLTCAVYGGSFSAYNWNWIRQP<br>PGKGLEWIGEINHRGDTAYNPSLKSRVTISVDTSKNQFSL<br>NLTSVTAADTAVYYCAARGYSYGWPPGYISDSFDYWGQGT<br>QVTVSS<br>SEQ ID NO: 25<br>CDR3: RGYSYGWPPGYISDSFDY (SEQ ID NO: 32) |

TABLE 2b -continued

Anti-PSMA $V_H$ amino acid sequences used in CAR constructs.

| $V_H$ | sequence |
|---|---|
| HB5 | QVQLQESGPGLVKPSQTLSLTCTVSGGSISNSGYYWSWVR<br>QHPGKDLEWIGFIYYNGSIHYNPSLKSRVIISVDTSKNQF<br>SLKMNSVTAADTAVYYCARDGDDYGDYLRGQGTLVTVSS<br>SEQ ID NO: 26<br>CDR3: DGDDYGDY (SEQ ID NO: 33) |

A control CAR construct was made using an anti-PSMA antibody reformatted as an scFv.
CDR3 sequences are shown in bold.

HB2 and HB 3 where shown in competition assays to bind to different epitopes on human PSMA.

CAR-T Cloning

Component parts were PCR amplified from human cDNA and joined by Gibson Assembly. Complete constructs were PCR amplified using tailed oligos containing attB1 sites, then shuttled via pDONR211 into Lentiviral destination plasmid pLenti6.3/V5-DEST by Gateway cloning (all Life Technologies) and standard molecular biology methods. Final constructs were sequence verified.

Oligos for amplifying CAR-T sequences for cloning into Lentiviral vector are shown below. All constructs use the same oligo pair. attB sequences are underlined, start/stop codons in bold.

TABLE 3

| Oligo name | Oligo sequence |
|---|---|
| CART-attB-F1 | GGGGACAAGTTTGTACAAAAAAGCAGGCTTCGAAGGA<br>GATAGAACCATGGCCTTACCAGTGACCGCCTTG<br>SEQ ID NO: 27 |
| CART-attB-R1 | GGGGACCACTTTGTACAAGAAAGCTGGGTTTAGCGAG<br>GGGGCAGGGCCTG<br>SEQ ID NO: 28 |

Example 2. Virus Production and Transduction

CAR-T constructs in pLenti6.3/V5-DEST were purified using the PureLink HQ plasmid purification kit (Life Technology). CAR-T plasmids were lipofected into 293-FT cells with ViraPower packaging plasmids (Life Technologies) according to the manufacturer's protocol. After 48-72 hours, cell supernatant containing live Lentivirus was harvested. Optionally, the virus was concentrated using Lenti-X Concentrator (Clontech), according to the manufacturer's protocol.

Jurkat E6.1 cells were grown in RPMI (Sigma), 10% foetal bovine serum, 2 mM L-glutamine Jurkat E6.1 cells were transduced for 48-72 hours with viral supernatant in a 50:50 mix of HEK cell supernatant:Jurkat medium: cells at a final concentration of $5 \times 10^5$/ml.

A non-CAR-T construct containing the open reading frame of the Green Fluorescent Protein (GFP) was included as a control. Note that this construct gives cytoplasmic expression.

Example 3. Analysis of Lentivirus Transduced T-Cells

Cells transduced with Lenti-GFP as explained above were analysed on a Sony SH800Z flow cytometer with 488 laser. Signal from GFP transduced cells was compared with untransduced cells. The results are shown in FIG. 5. This demonstrates that transduction works.

Constructs expressing irrelevant $V_H$ with a HIS tag were shown by flow cytometry to have surface expression on Jurkat cells using anti-His detection agents. This shows that the leader sequence directs the CART to the surface of the cell as expected.

Example 4. Functional Activity in Cell Assay

Chimeric antigen receptor constructs comprising a $V_H$ domain as the binding domain expressed in Jurkat cells were tested for the functional activity by measurement of secreted IL-2 levels following stimulation with PSMA expressing cells or control cell lines.

CHO TREX human PSMA cells (25000 cells/well) were seeded into white 96 well tissue culture treated assay plates in Nutrient mix HAMs F12 media containing 10% FBS, 2 mM L-Glutamine, 10 ug/ml Blasticidin, 300 ug/ml Zeocin, 1×Pen/Strep, 1 ug/ml Tetracycline. Control cell lines (CHO TREX parent cells and CHO TREX cells stably expressing a TCR activator) were seeded into the assay plates in Nutrient mix HAMs F12 media containing 10% FBS, 2 mM L-Glutamine, 10 ug/ml Blasticidin, 1×Pen/Strep. Plates were incubated for 24 hours at 37° C. in a $CO_2$ incubator.

The media was removed from the wells and replaced with 50 ul assay media (RPMI supplemented with 10% FBS, 2 mM L-Glutamine and 1×Pen/Strep). Jurkat cells expressing the VH chimeric antigen receptor or non-transduced Jurkats were diluted to 1e6 cells/ml and 50 ul added to the wells. Plates were incubated for 24 or 48 hours at 37° C. in a $CO_2$ incubator then IL-2 levels in the supernatants were quantified using the CisBio Human IL-2 assay kit (cat no. 64IL2PEB) according to the manufacturers' instructions.

Stimulation of Jurkats expressing PSMA $V_H$ chimeric antigen receptor with CHO PSMA cells resulted in IL-2 levels substantially higher compared to background (stimulation with CHO TREX parent cells) or control cells (non-PSMA binding) confirming PSMA mediated cell signalling in these cells. The IL-2 levels were comparable to those obtained by direct stimulation of the T-cell receptor complex through a cell expressed TCR activator molecule.

Figure 7:
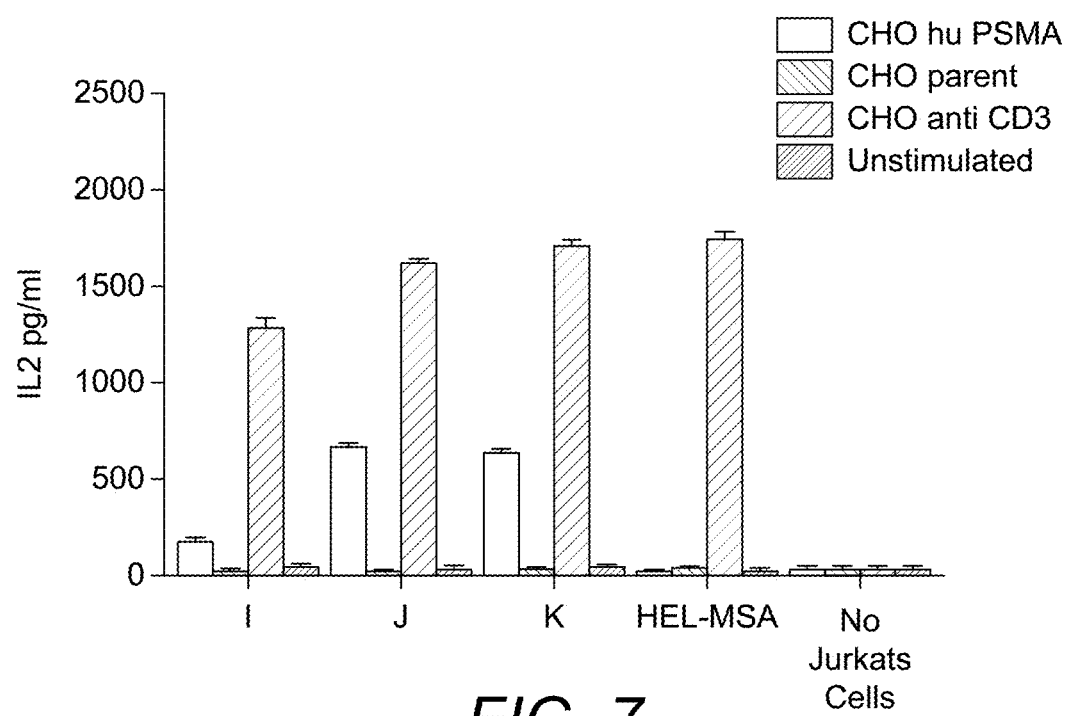

The results are illustrated in FIGS. 6 and 7. FIGS. 6a and 6b show PSMA mediated stimulation of IL-2 secretion from Jurkat cells expressing PSMA $V_H$ CAR constructs containing one PSMA binding VH per receptor, positive PSMA binding antibody fragment control construct, a non PSMA binding $V_H$ chimeric antigen receptor construct (HEL-Ig) or GFP. Cells were stimulated for 24 hours with CHO human PSMA expressing cells, CHO TREX parent cells (untransfected), CHO cells expressing a TCR activator or media only (unstimulated). Il2 release is only seen in response to PSMA binding.

FIG. 7 shows PSMA mediated stimulation of IL-2 secretion from Jurket cells expressing CAR constructs with two $V_H$ per receptor, either bispecific (HB3-HB3), biparatopic (HB2-HB3) or one PSMA binding $V_H$ and one irrelevant $V_H$ (HB3-MSA). Il-2 levels were substantially higher than background or than an similar CAR containing two irrelevant $V_H$ (HEL-MSA.

The invention claimed is:

1. An isolated chimeric antigen receptor (CAR) comprising an antigen binding domain, a transmembrane domain and an intracellular signalling domain wherein said binding domain comprises a first single human variable heavy chain ($V_H$) domain antibody that comprises SEQ ID NO. 23 or 24, and a second single human variable heavy chain ($V_H$) domain antibody wherein said first single human VH domain antibody binds to human Prostate-specific membrane antigen (PSMA) and said second single human VH domain antibody binds to a second target.

2. The CAR according to claim 1 wherein the second single human variable heavy chain ($V_H$) domain antibody binds to human PSMA and comprises SEQ ID NO. 23 or 24.

3. The CAR according to claim 1 wherein said single human variable heavy chain ($V_H$) domain antibody has been generated from a human variable heavy chain in a triple knock out mouse in which the heavy chain, kappa light and lambda light chain loci are functionally silenced.

4. An isolated nucleic acid encoding a CAR according to claim 1 or a vector comprising said nucleic acid.

5. An isolated cell or cell population comprising one or more CAR as defined in claim 1.

6. A pharmaceutical composition comprising a cell or cell population as defined in claim 5 and a pharmaceutical acceptable carrier, excipient or diluent.

7. A method for treating cancer in a subject, for stimulating a T cell-mediated immune response to a target cell population or tissue in a subject, or for providing an anti-tumor immunity in a subject, the method comprising administering to the subject a cell or cell population according to claim 5, a cell or cell population genetically modified to express a CAR as defined in claim 1, or a pharmaceutical composition according to claim 6.

8. The method according to claim 7, wherein the cancer is selected from a haematological cancer, a solid cancer or prostate cancer.

9. An ex vivo method for generating a population of cells for use in adaptive immunotherapy comprising transforming said cell with a nucleic acid encoding a CAR as defined in claim 4 or a vector according to claim 4.

10. A CAR according to claim 1 wherein said second target is a tumour antigen.

11. A CAR according to claim 1 wherein said second target is selected from PSCA, BCMA, CS1, GPC3, CSPG4, EGFR, CD123, 5T4, CD23, L1 CAM, MUC16, ROR1, SLAMF7, cKit, CD19, CD20, CD22, CD33, CD38, CD53, CD92, CD100, CD148, CD150, CD200, CD261, CD262, CD362, ROR1, mesothelin, CD33/IL3Ra, c-Met, Glycolipid F77, EGFRvlll, GD-2, NY-ESO-1 TCR or MAGE A3 TCR, human telomerase reverse transcriptase (hTERT), survivin, cytochrome P450 1 B1 (CY1 B), HER2, Wilm's tumor gene 1 (WT1), livin, alphafetoprotein (AFP), carcinoembryonic antigen (CEA), mucin 16, MUC1, p53 and cyclin.

12. A CAR according to claim 1 wherein said second target is an immuno checkpoint target.

13. An isolated chimeric antigen receptor (CAR) comprising an antigen binding domain, a transmembrane domain and an intracellular signaling domain wherein said binding domain comprises a first single human variable heavy chain (VH) domain antibody that comprises SEQ ID NO. 23 or 24 and second single human variable heavy chain (VH) domain antibody that comprises SEQ ID NO. 23 or 24, wherein said first and second single human VH domain antibody bind to human Prostate-specific membrane antigen (PSMA).

* * * * *

UNITED STATES PATENT AND TRADEMARK OFFICE
CERTIFICATE OF CORRECTION

PATENT NO. : 11,866,510 B2
APPLICATION NO. : 16/099099
DATED : January 9, 2024
INVENTOR(S) : McGuinness et al.

It is certified that error appears in the above-identified patent and that said Letters Patent is hereby corrected as shown below:

On the Title Page

(56) References Cited, OTHER PUBLICATIONS, BAYACHOU, MEKKI, et al. cite: Please correct BAYACHOU, MEKKI, et al., ""Catalytic Two-Electron Reductions of N2) and N3 by My globin in Surfactant Films" Inorg. Chemn. 2000, 39, 289-293." to read --BAYACHOU, MEKKI, et al., ""Catalytic Two-Electron Reductions of $N_2O$ and $N_3^-$ by Myoglobin in Surfactant Films" Inorg. Chem. 2000, 39, 289-293."--

(56) References Cited, OTHER PUBLICATIONS, CHATALIC, KRISTEN, et al. cite: Please correct "A Novel In-Labeled Anti-Prostate-Specific Membrane Antigen Nanobody for Targeted SPECT/CT Imaging ofProstate Cancer" to read --A Novel In-Labeled Anti-Prostate-Specific Membrane Antigen Nanobody for Targeted SPECT/CT Imaging of Prostate Cancer--

(56) References Cited, OTHER PUBLICATIONS, FATEMEH RAHIMI JAMNANI, et al. cite: Please correct "T cells expressing VHH-directed oligoclonal chimeric HER2 antigen receptors: Towards tumor-directed oligocional T cell therapy" to read --T cells expressing VHH-directed oligoclonal chimeric HER2 antigen receptors: Towards tumor-directed oligoclonal T cell therapy--

(56) References Cited, OTHER PUBLICATIONS, MATTHIAS DI HUYVETTER, et al. cite: Please correct "Radiolabeled nanobodies as theranostic tools in targeted radionuclide therapy off cancer" to read --Radiolabeled nanobodies as theranostic tools in targeted radionuclide therapy of cancer--

(56) References Cited, OTHER PUBLICATIONS, MNCKE, CECILE, et al. cite: Please correct "MNCKE, CECILE , et al." to read --VINCKE, CECILE , et al.--

In the Specification

Column 5, Line 37: Please correct "domain or" to read --domain" or--

Signed and Sealed this
Ninth Day of April, 2024

Katherine Kelly Vidal
*Director of the United States Patent and Trademark Office*

CERTIFICATE OF CORRECTION (continued)
U.S. Pat. No. 11,866,510 B2

Column 8, Line 21: Please correct "bispecifc" to read --bispecific--

Column 8, Line 41: Please correct "at least two, at least, at least three," to read --at least two, at least three,--

Column 8, Line 54: Please correct "such the" to read --such that the--

Column 11, Line 59: Please correct "EGFRvII" to read --EGFRvIII--

Column 12, Line 50: Please correct "F" to read --ε--

Column 17, Line 38: Please correct "RNA:" to read --RNA;--